(12) United States Patent
 Tsuchiya et al.

(10) Patent No.: US 9,394,521 B2
(45) Date of Patent: Jul. 19, 2016

(54) CELL PREPARATION CONTAINING MESENCHYMAL STEM CELLS, AND METHOD FOR PRODUCING SAME

(75) Inventors: Toshie Tsuchiya, Tokyo (JP); Koichiro Tsuji, Hiroshima (JP); Yukio Kato, Hiroshima (JP); Jin Chang Shao, Hiroshima (JP); Maiko Hara, Hiroshima (JP)

(73) Assignee: TWO CELLS Co., Ltd., Hiroshima (JP)

( * ) Notice: Subject to any disclaimer, the term of this patent is extended or adjusted under 35 U.S.C. 154(b) by 0 days.

(21) Appl. No.: 13/583,150

(22) PCT Filed: Mar. 10, 2011

(86) PCT No.: PCT/JP2011/055683
 § 371 (c)(1),
 (2), (4) Date: Sep. 6, 2012

(87) PCT Pub. No.: WO2011/111787
 PCT Pub. Date: Sep. 15, 2011

(65) Prior Publication Data
 US 2012/0329087 A1 Dec. 27, 2012

(30) Foreign Application Priority Data

Mar. 10, 2010 (JP) .............................. 2010-053179

(51) Int. Cl.
 *C12N 5/0775* (2010.01)
 *C12Q 1/06* (2006.01)
 *A61K 35/12* (2015.01)

(52) U.S. Cl.
 CPC ............ *C12N 5/0663* (2013.01); *C12N 5/0668* (2013.01); *A61K 35/12* (2013.01); *C12N 2500/90* (2013.01); *C12N 2501/11* (2013.01); *C12N 2501/115* (2013.01); *C12N 2501/12* (2013.01); *C12N 2501/135* (2013.01); *C12N 2501/15* (2013.01)

(58) Field of Classification Search
 None
 See application file for complete search history.

(56) References Cited

U.S. PATENT DOCUMENTS

| | | | |
|---|---|---|---|
| 6,617,159 | B1 | 9/2003 | Cancedda et al. |
| 7,109,032 | B2 | 9/2006 | Cancedda et al. |
| 7,169,610 | B2 | 1/2007 | Brown |
| 2003/0143737 | A1 | 7/2003 | Morrison et al. |
| 2003/0211604 | A1 | 11/2003 | Brown |
| 2005/0013804 | A1 * | 1/2005 | Kato et al. ............... 424/93.7 |
| 2005/0032122 | A1 | 2/2005 | Hwang et al. |
| 2005/0090002 | A1 | 4/2005 | Cancedda et al. |
| 2005/0132426 | A1 | 6/2005 | Morrison et al. |
| 2005/0265980 | A1 | 12/2005 | Chen et al. |
| 2005/0272152 | A1 | 12/2005 | Xu et al. |
| 2006/0216821 | A1 | 9/2006 | Totey et al. |
| 2007/0275463 | A1 | 11/2007 | Brown |
| 2009/0202654 | A1 | 8/2009 | Nixon |
| 2010/0279412 | A1 | 11/2010 | Kato et al. |

FOREIGN PATENT DOCUMENTS

| | | |
|---|---|---|
| EP | 0 274 445 B1 | 7/1993 |
| EP | 1988159 A1 * | 11/2008 |
| JP | 08-308561 | 11/1996 |
| JP | 09/191874 | 7/1997 |
| JP | 2002-529071 | 9/2002 |
| JP | 2003-516141 | 5/2003 |
| JP | 2005-515777 | 6/2005 |
| JP | 2007-00077 A | 1/2007 |
| WO | 97/34614 | 9/1997 |
| WO | 99/47163 A2 | 9/1999 |
| WO | 03/104442 | 12/2003 |
| WO | 2004/069172 A2 | 8/2004 |
| WO | 2007/080919 A1 | 7/2007 |
| WO | 2009/114860 A2 | 9/2009 |

OTHER PUBLICATIONS

Kato et al. WO 2007/080919, JPO machine translation.*
Burns et al. "Tumorigenic heterogeneity in cancer stem cells evolved from long-term cultures of telomerase-immortalized human mesenchymal stem cells", Cancer Research 65(8): 3126-35, 2005.*
Clyman et al. "Integrin receptors on aortic smooth muscle cells mediate adhesion to fibronectin, laminin, and collagen", Circulation Research 67: 175-186, 1990.*
Kao et al. "Trypzean™: recombinant bovine trypsin expressed in corn—a non-animal alternative" SIGMA® Technical Articles, available online, published Jan. 2004.*
Chen et al. "Extracellular matrix made by bone marrow cells facilitates expansion of marrow-derived mesenchymal progenitor cells and prevents their differentiation into osteoblasts", Journal of Bone and Mineral Research 22(12): 1943-1956, 2007.*
Stem Cell Research "The next revolution in MSC culture: STEMPRO MSC SFM serum-free human mesenchymal stem cell culture medium", Invitrogen, available from company webpage <<www.invitrogen.com>>, copyright 2008.*
Summons to Attend Oral Proceedings Pursuant to Rule 115(1) EPC for corresponding Application No. EP 07706579.5 dated Oct. 25, 2012.
Lee et al., Blood vol. 103, Mar. 1, 2004, pp. 1669-1675.
Office Action dated Mar. 29, 2013 corresponding to U.S. Appl. No. 12/160,481.
Advisory Action issued to corresponding U.S. Appl. No. 13/127,774 dated May 10, 2013.

(Continued)

*Primary Examiner* — Emily Cordas
(74) *Attorney, Agent, or Firm* — Renner, Otto, Boiselle & Sklar, LLP

(57) ABSTRACT

A cell preparation containing mesenchymal stem cells whose immunosuppression ability is maintained is produced by means of a serum-free or low-serum culture. A method for producing a cell preparation containing mesenchymal stem cells, comprising the steps of: (A) proliferating mesenchymal stem cells in a serum-free medium "A" containing an FGF, a PDGF, a TGF-β, an HGF, an EGF, at least one phospholipid, and at least one fatty acid; and (B) screening mesenchymal stem cells whose immunosuppression ability is maintained or improved, from the mesenchymal stem cells thus proliferated in the step (A).

10 Claims, 10 Drawing Sheets

(56) References Cited

OTHER PUBLICATIONS

International Search Report for corresponding International Application No. PCT/JP2011/055683 mailed Apr. 5, 2011.
Form PCT/ISA/237 for corresponding International Application No. PCT/JP2011/055683 dated Apr. 5, 2011.
Y Kato, "Development of Serum-free Medium for Human Mesenchymal Stem Cells", Iryokiki Forum (Medical Equipment Forum), 33-35, 2007 and full English translation.
Armand Keating, "How Do Mesenchymal Stromal Cells Suppress T Cells?", Cell Stem Cell, 2, pp. 106-108, 2008.
Corcione et al., "Human mesenchymal stem cells modulates B-cell functions", Blood 107, pp. 367-372, 2006.
Ramasamy et al., "Mesenchymal Stem Cells Inhibit Dendritic Cell Differentiation and Function by Preventing Entry Into the Cell Cycle", Transplantation 83, No. 1, pp. 71-76, 2007.
Aggarwal et al., "Human mesenchymal stem cells modulate allogeneic immune cell responses", Blood 105, pp. 1815-1822, 2005.
Le Blanc et al., "Immunomodulation by mesenchymal stem cells and clinical experience", Journal of Internal Medicine, 262, pp. 509-525, 2007.
Djouad et al., "Immunosuppressive effect of mesenchymal stem cells favors tumor growth in allogeneic animals", Blood 102, pp. 3837-3844, 2003.
Y. Kato, "Active Stemness Molecular Mechanism of Mesenchymal Stem Cells in Serum-free Medium: Diversion from serum regenerative medicine to serum-free regenerative medicine", Research Council Meeting of Japan Society of Plastic and Reconstructive Surgery, 2009, vol. 18th, pp. 54-55 and full English translation.
Sawada et al., "Gene Expression Changes in Human Bone-marrow Derived Mesenchymal Stem Cells during the in vitro Culture-Influence of Serum-free Medium", Regenerative Medicine, 2009, vol. 8, No. suppl, p. 248 and full English translation.
Doucet et al., "Platelet Lysates Promote Mesenchymal Stem Cell Expansion: A Safety Substitute for Animal Serum in Cell-Based Therapy Applications", Journal of Cellular Physiology, 2005, vol. 205, pp. 228-236.
Sotiropoulou et al., "Characterization of the Optimal Culture Conditions for Clinical Scale Production of Human Mesenchymal Stem Cells", STEM CELLS, 2006, vol. 24, pp. 462-471.
Di Nicola et al., "Human bone marrow stromal cells suppress T-lymphocyte proliferation induced by cellular or nonspecific mitogenic stimuli", Blood, 2002, vol. 99, No. 10, pp. 3838-3843.
International Search Report for corresponding International Application No. PCT/JP2007/050232 mailed Mar. 20, 2007.
Hideki Jamaji et al., "Promoting effect of phospholipid on proliferation of CHO cells in serum free culturing", Abstracts of presentations for the Muroran Meeting of the Society of Chemical Engineering, Japan, at Muroran Institute of Technology, Aug. 6-7, 1998; p. 140. (Includes partial English translation).
Regina Labitzke et al.; "A serum-free medium formulation supporting growth of human umbilical cord vein endothelial cells in long-term cultivation"; Cytotechnology, 35; pp. 87-92, 2001.
Emily Shacter; "Serum-free medium for growth factor-dependent and—independent plasmacytomas and hybridomas"; Journal of Immunological Methods, 99; pp. 259-270; 1987.
Chiyo Hori et al.; "Induction of lithium ion of multiplication of mouse mammary epithelium in culture"; Proc. Natl Acad. Sci. USA; vol. 76, No. 6; pp. 2823-2827; Jun. 1979.
Kentaro Sakai et al.; "Use of Nonionic Surfactants for Effective Supply of Phosphatidic Acid in Serum-Free Culture of Chinese Hamster Ovary Cells"; Journal of Bioscience and Bioengineering; vol. 92, No. 3; pp. 256-261; 2001.
Yoshiro Saito et al., "III-14 Research on Effect of Essential Micronutrient Selenium on Cell Survival"; Proceedings of the Japanese Conference on the Biochemistry of Lipids; vol. 45; pp. 262-265; 2003. (Includes partial English translation).
Ben J. Walthall et al.; "Multiplication of Human Diploid Fibroblasts in a Synthetic Medium Supplemented with EGF; Insulin, and Dexamethoasone"; Experimental Cell Research, 134; pp. 303-311; 1981.
European Search Report for corresponding Application No. 07706579.5 dated Apr. 2, 2009.
Forte Giancarlo et al.; "Hepatocyte growth factor effects on mesenchymal stem cells: proliferation, migration, and differentiation"; STEM CELLS; Jan. 2006, vol. 24, No. 1; pp. 23-33.
Korean Office Action for corresponding Korean Application No. 10-2008-7019812 dated Oct. 11, 2010 (with English translation).
Sandstorm et al., "Review: Serum-Free Media for Cultures of Primitive and Mature Hematopoietic Cells", Biotechnology and Bioengineering, 1994, vol. 43, pp. 706-733.
Neuss et al., "Functional Expression of HGF and HFG Receptor/c-met in Adult Human Mesenchymal Stem Cells Suggests a Role in Cell Mobilization, Tissue Repair, and Wound Healing", Stem Cells, 2004, 22, pp. 405-414.
US Office Action dated Mar. 30, 2011 for corresponding U.S. Appl. No. 12/160,481.
US Office Action dated Sep. 15, 2011 for corresponding U.S. Appl. No. 12/160,481.
US Office Action dated Jun. 5, 2012 for corresponding U.S. Appl. No. 12/160,481.
US Office Action dated Oct. 9, 2012 for corresponding U.S. Appl. No. 12/160,481.
International Search Report for corresponding International Application No. PCT/JP2009/005573 mailed Dec. 15, 2009.
Kratchmarova et al., "Mechanism of Divergent Growth Factor Effects in Mesenchymal Stem Cell Differentiation", Science (2005), vol. 308, p. 1472-1477.
Misawa et al., "Haisei Kensaibo o Mochiita Saisei," Organ Biology (2005), vol. 12, No. 4, pp. 281-289 with machine translation.
Campagnoli et al., "Identification of mesenchymal stem/progenitor cells in human first-trimester fetal blood, liver, and bone marrow", Blood (2001), vol. 98, No. 8, p. 2396-2402.
Supplementary European Search Report for corresponding European Application No. EP 09 82 5870 mailed Mar. 21, 2012.
Kotev-Emeth et al., "Establishment of a Rat Long-Term Culture Expressing the Osteogenic Phenotype: Dependence on Dexamethasone and FGF-2", Connective Tissue Research, 2002, vol. 43, pp. 606-612.
Maegawa et al., "Enhancement of osteoblastic differentiation of mesenchymal stromal cells cultured by selective combination of bone morphogenetic protein-2 (BMP-2) and fibroblast growth factor-2 (FGF-2)", Journal of tissue engineering and regenerative medicine, 2007, vol. 1, pp. 306-313.
Chaudhary et al., "Differential growth factor control of bone formation through osteoprogenitor differentiation", Bone, 2004, vol. 34, pp. 402-411.
Frank et al., "Real-Time Quantitative RT-PCR Analysis of Human Bone Marrow Stromal Cells During Osteogenic Differentiation in Vitro", Journal of Cellular Biochemistry, 2002, vol. 85, pp. 737-746.
Friedman et al., "Osteogenic Differentiation of Human Mesenchymal Stem Cells is Regulated by Bone Morphogenetic Protein-6", Journal of Cellular Biochemistry, 2006, vol. 98, pp. 538-554.
US Office Action dated Oct. 2, 2012 for corresponding U.S. Appl. No. 13/127,774.
Shioi et al., "β-Glycerophosphate Accelerates Calcification in cultured Bovine Vascular Smooth Muscle Cells", Arteriosclerosis, Thrombosis, and Vascular Biology, 1995; 15:2003-2009.
Office Action dated Feb. 27, 2013 from co-pending U.S. Appl. No. 13/127,774.
Extended European Search Report dated Aug. 2, 2013 in European Application No. 11753445.3.
Office Action for corresponding U.S. Appl. No. 12/160,481 dated Oct. 21, 2013.
Gregory et al., Journal of Biological Chemistry, vol. 280: "Dkk-1-derived Synthetic Peptides and Lithium Chloride for the Control and Recovery of Adult Stem Cells from Bone Marrow", pp. 2309-2323, dated Jan. 21, 2005.
Lee et al., "Tumorigenesis Study of Canine Adipose Derived-mesenchymal Stem Cell", Journal of Toxicology and Public Health, Sep. 21, 2007, pp. 271-278, vol. 23, No. 3, with English translation thereof.
Yañez et al., "Adipose Tissue-Derived Mesenchymal Stem Cells Have in Vivo Immunosuppressive Properties Applicable for the Con-

(56) References Cited

OTHER PUBLICATIONS trol of the Graft-Versus-Host Disease", Stem Cells, Jul. 27, 2006, pp. 2582-2591, vol. 24, AlphaMed Press.
Office Action for corresponding Korean Application No. 10-2012-7026184, dated Nov. 29, 2013, with English translation thereof.
Office Action for co-pending U.S. Appl. No. 13/127,774 dated Dec. 6, 2013.
Valta et al., "Regulation of Osteoblast Differentiation: A Novel Function for Fibroblast Growth Factor 8", Endocrinology, May 2006, 147(5), pp. 2171-2182.
Broedel, Jr. et al., "The Case for Serum-Free Media", BioProcess International, Feb. 2003, pp. 56-58.
Singh et al., "Parathyroid Hormone Stimulates Phosphatidylethanolamine Hydrolysis by Phospholipase D in Osteoblastic Cells", Lipids, Nov. 2005, 40(11), pp. 1135-1140.
Pasco et al., "Antioxidant Vitamin Supplements and Markers of Bone Turnover in a Community Sample of Nonsmoking Women", Journal of Women's Health, 2006, 15(3), pp. 295-300.
Final Office Action for related U.S. Appl. No. 12/160,481 dated Sep. 16, 2014.
Advisory Action for co-pending U.S. Appl. No. 13/127,774, dated Jul. 31, 2014.
Final Office Action for co-pending U.S. Appl. No. 13/127,774 dated May 8, 2014.
Office Action for related U.S. Appl. No. 12/160,481 dated Jun. 4, 2014.
Advisory Action for co-pending U.S. Appl. No. 12/160,481 dated Jan. 7, 2014.
Peter et al. "Osteoblastic phenotype of rat marrow stromal cells cultured in the presence of dexamethasone, beta-glycerolphosphate, and L-ascorbic acid", Journal of Cellular Biochemistry, 1998;71:55-62.
Office Action for co-pending U.S. Appl. No. 13/127,774, dated Dec. 19, 2014.
Advisory Action for co-pending U.S. Appl. No. 12/160,481, dated Jan. 22, 2015.
Advisory Action for co-pending U.S. Appl. No. 13/127,774, dated Sep. 29, 2015.
Final Office Action for co-pending U.S. Appl. No. 13/127,774 dated Jul. 17, 2015.
Office Action for related U.S. Appl. No. 14/885,134, dated Mar. 16, 2016.

\* cited by examiner

MEDIUM 1          10%FBS-MEM

CELL PREPARATION CONTAINING MESENCHYMAL STEM CELLS, AND METHOD FOR PRODUCING SAME

TECHNICAL FIELD

The present invention relates to a cell preparation containing mesenchymal stem cells and a method for producing the same. The present invention further relates to an additive for a medium for use in the method, a culturing medium, a kit, and a culturing method using any one of them.

BACKGROUND ART

Mesenchymal stem cells (MSCs) can be isolated not only from tissues of adults, such as bone marrow, fat, a synovial membrane, an alveolar bone, and a peridontal membrane, but also from various cells, such as placenta, cord blood, and umblical cord. In addition, the mesenchymal stem cells can be cultured and proliferated in vitro. Furthermore, the mesenchymal stem cells have multipotency so that the mesenchymal stem cells can be differentiated not only to a plurality of mesenchymal cells (osteoblast, fat cell, cartilage cell), but also to non-mesenchymal cells (neural precursor cell, hepatocyte). Accordingly, the mesenchymal stem cells are expected to be applicable as a cell source for regenerative medicine and cell treatment.

A medium containing fetal bovine serum (FBS) has been conventionally used for culturing mesenchymal stem cells. Bovine serum has lot differences, and in addition, causes an immune response in transplantation because the use of bovine serum results in contamination of the mesenchymal stem cells with a serum protein derived from a heterozonic. It is difficult to stably culture the mesenchymal stem cells even by use of human serum due to individual differences. Further, this culturing gives a large physical burden to a donor, and costs a large amount of money.

Therefore, it is known that, in order to supply mesenchymal stem cells which are safer and has a stable quality, a serum-free medium with which no or little contamination with a protein derived from a heterozonic occurs during culturing is suitable. That is, it is preferable that the mesenchymal stem cells are proliferated by a serum-free culturing. Patent Literature 1 and Non-patent Literature 1 disclose serum-free culturing of mesenchymal stem cells. The serum-free culturing mesenchymal stem cells as described in Patent Literature 1 and Non-patent Literature 1 produce a proliferation promoting effect superior to that of culturing of mesenchymal stem cells with a 5 to 15% FBS-containing medium. Such serum-free culturing also allows to produce mesenchymal stem cells whose multipotency is maintained (improved).

It has been known that mesenchymal stem cells not only have low immunogenicity, but also affect functions of various immune effecter cells (T cell, B cell, NK cell, dendritic cell) (see Non-patent Literatures 2 to 5). Accordingly, the mesenchymal stem cells are expected to be applicable to treatment for various diseases relating to immune responses (Non-patent Literature 6). Non-patent Literature 7 discloses that mesenchymal stem cells down-regulate proliferation of T cells caused by a mouse mixed lymphocyte reaction (MLR).

CITATION LIST

Patent Literature

Citation List
  Patent Literature 1
    Pamphlet of International Publication WO2007/080919 (Publication date: Jul. 19, 2007)
  Non Patent Literature
    Non Patent Literature 1
      KATO Yukio, Proceedings of Fifth Iryokiki Forum (Medical Equipment Forum), 33-35, 2007
    Non Patent Literature 2
      Keating, A., Cell Stem Cell, 2, 106-108, 2008
    Non Patent Literature 3
      Corcione, A. et. al., Blood 107, 367-372, 2006
    Non Patent Literature 4
      Ramasamy, R. et. al., Transplantation 83, 71-76, 2007
    Non Patent Literature 5
      Aggarwal, S. et. al., Blood 105, 1815-1822, 2005
    Non Patent Literature 6
      Le Blanc K. et. al., J Intern Med., 262, 509-525, 2007
    Non Patent Literature 7
      Djouad, F. et. al., Blood 102, 3837-3844, 2003

SUMMARY OF INVENTION

Technical Problem

Immunorejection in transplantation is an important problem in regenerative medicine, and an immunosuppressant is used to prevent the immunorejection. The use of immunosuppressant is, however, associated with problems such as a side effect of the immunosuppressant. Mesenchymal stem cells have immunosuppression ability, so that the immunosuppressant is not necessary if the mesenchymal stem cells can be used. Therefore it would be advantageous if mesenchymal stem cells having immunosuppression ability was produced by carrying out serum-free or low-serum culturing having a low risk of heteroprotein and a synthetic medium contamination. Particularly, an FBS-containing medium has a problem not only in an amount of bovine serum albumin but also in containing other soluble allergic substances. It is therefore necessary to use a culturing medium which does not contain bovine serum albumin and the other soluble substances.

The present invention has been made in view of the aforementioned problem, and an object of the present invention is to provide a method for producing a cell preparation containing mesenchymal stem cells whose immunosuppression ability is maintained by carrying out the serum-free or low-serum culturing.

Solution to Problem

In order to attain the aforementioned object, the inventors of the present invention diligently studied influence of serum-free culture on immunosuppression ability of mesenchymal stem cells. As a result, the inventors found that the mesenchymal stem cells cultured in a serum-free medium containing a particular additive maintains immunosuppression ability, and an immunosuppressive effect is even improved. Based on this finding, the present invention was accomplished.

Specifically, a method for producing a cell preparation containing mesenchymal stem cells according to the present invention includes the steps of: (A) proliferating mesenchymal stem cells in a serum-free medium "A" containing an FGF, a PDGF, a TGF-β, an HGF, an EGF, at least one phospholipid, and at least one fatty acid; and (B) screening mesenchymal stem cells whose immunosuppression ability is maintained or improved, from the mesenchymal stem cells thus proliferated in the step (A).

A cell preparation containing mesenchymal stem cells according to the present invention is produced by the aforementioned producing method.

A serum-free additive for a medium for producing a cell preparation containing mesenchymal stem cells whose immunosuppression ability is maintained or improved, comprising: an FGF; a PDGF; a TGF-β; an HGF; an EGF; at least one phospholipid; and at least one fatty acid.

A serum-free culturing medium according to the present invention is a culturing medium for producing a cell preparation containing mesenchymal stem cells whose immunosuppression ability is maintained or improved, comprising: the additive for a medium.

A culture method according to the present invention for producing a cell preparation containing mesenchymal stem cells whose immunosuppression ability is maintained or improved, comprising: (F) culturing mesenchymal stem cells in the culturing medium.

A kit according to the present invention for producing a cell preparation containing mesenchymal stem cells whose immunosuppression ability is maintained or improved, comprising at least: the additive "A" for a medium.

Advantageous Effects of Invention

A method for producing a cell preparation containing mesenchymal stem cells according to the present invention, comprising the steps of: (A) proliferating mesenchymal stem cells in a serum-free medium "A" containing an FGF, a PDGF, a TGF-β, an HGF, an EGF, at least one phospholipid, and at least one fatty acid; and (B) screening mesenchymal stem cells whose immunosuppression ability is maintained or improved, from the mesenchymal stem cells thus proliferated in the step (A).

For a fuller understanding of the nature and advantages of the invention, reference should be made to the ensuing detailed description taken in conjunction with the accompanying drawings.

DESCRIPTION OF EMBODIMENTS

Figure 1:
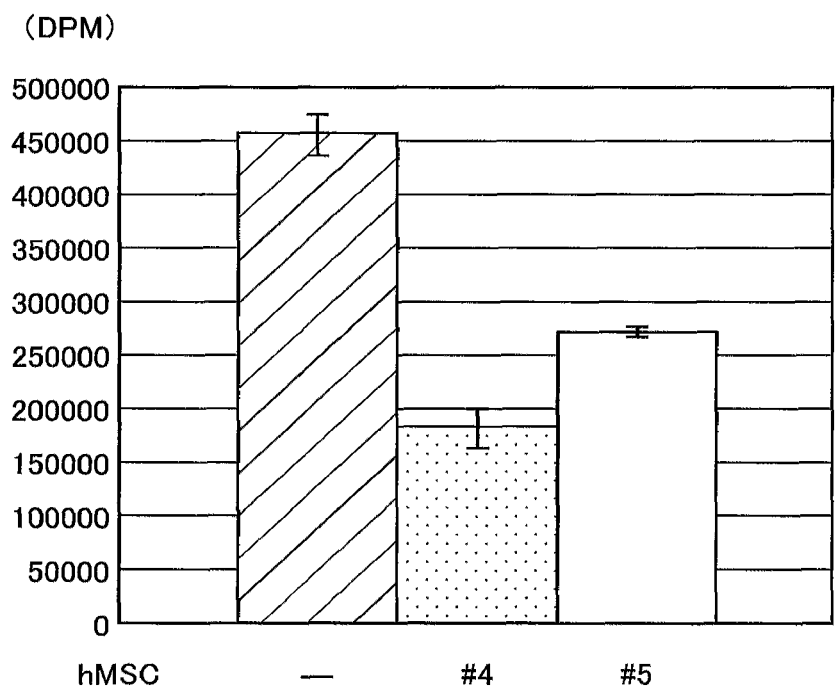
FIG. 1 is a graph showing an immunosuppressive effect of hMSCs on anti-CD3 and anti-CD28 stimulation T cell proliferative responses in a case where an activated mouse T cell and the hMSC were co-cultured in an MSCGM medium.

One embodiment of the present invention is described below in detail. Note, however, that the present invention is not limited thereto. The present invention can be modified in many ways within the scope of the description. Note that "A to B" indicative of a numerical range means "A or more and B or less", unless otherwise specified in the Specification.

As described above, Patent Literature 1 and Non-patent Literature 1 disclose a medium (serum-free medium) which does not contain serum and which allows to culture cells without loosing proliferation ability. The medium is made by adding, to a basal medium, a complex of a particular growth factor group, a phospholipid, and a fatty acid, thereby giving the medium a cell proliferation promoting effect equal to or larger than that of a medium under a 10% serum condition, even if the medium is a serum-free medium. It is possible to carry out serum-free culturing of mesenchymal stem cells in the medium while maintaining or improving differentiation ability of the mesenchymal stem cells. It is also possible to carry out serum-free culturing of MSCs derived from bone marrow, MSCs derived from fat, and MSCs derived from the synovial membrane in the medium.

According to the present invention, a medium having ability of greatly proliferating the mesenchymal stem cells under the serum-free condition further has an effect of realizing culture of the mesenchymal stem cells whose immunosuppression ability is maintained or improved. This makes it possible to produce a cell preparation containing the mesenchymal stem cells which are useful for regenerative medicine in particular.

(1) Method for Producing Cell Preparation Containing Mesenchymal Stem Cells

The present invention provides a method for producing a cell preparation containing mesenchymal stem cells whose immunosuppression ability is maintained or improved under a serum-free condition. The method for producing the cell preparation according to the present invention includes the steps of: (A) proliferating mesenchymal stem cells in a serum-free medium "A" containing an FGF, a PDGF, a TGF-β, an HGF, an EGF, at least one phospholipid, and at least one fatty acid; and (B) screening mesenchymal stem cells whose immunosuppression ability is maintained or improved from the mesenchymal stem cells thus proliferated which have been subjected to the step (A).

(Proliferation Step)

In a proliferation step of this producing method according to the present invention, the mesenchymal stem cells are proliferated by culturing the mesenchymal stem cells in a serum-free medium "A" containing an FGF, a PDGF, a TGF-β, an HGF, an EGF, at least one phospholipid, and at least one fatty acid.

In the Specification, the term "serum-free medium" means a medium which does not contain serum, and the term "serum-free culturing" is culturing without serum. Further, in the Specification, the term "low-serum culturing" means culturing by use of a medium whose serum content is lower than that of a general serum-containing medium (e.g., 10% FBS-containing medium), and also means culturing whose culturing period by use of a serum-containing medium is shorter than that of general culturing by use of the serum-containing medium.

In the Specification, the term "cell preparation" is a remedy made by preparing a cell, and is used for regenerative medicine etc. as a material for regenerative medicine. The term "cell preparation" encompasses not only a preparation made by preparing a cell as it is, i.e., a cell whose functions are not changed, but also a preparation made by preparing a cell whose functions (such as a differentiation ability and an immunosuppression ability) are improved by culturing and proliferating the cell under a particular condition.

Further, in the Specification, the term "mesenchymal stem cells" encompasses not only cells isolated from tissues of adults, such as bone marrow, a fat cell, a synovial cell, a alveolar bone, and a peridontal membrane, but also cells isolated from various cells such as fetus, placenta, and cord blood. It is preferable that the term "mesenchymal stem cells" are human mesenchymal stem cells, however, mesenchymal stem cells derived from non-human animals, such as rats and mice, may be used.

A basal medium for constituting the serum-free medium "A" for use in the proliferation step is not particularly limited, provided that the basal medium is a well-known medium for animal cells in this field. A preferable examples of the basal medium encompass a Ham's F12 medium, a DMEM medium, an RPMI-1640 medium, and an MCDB medium. Those basal mediums can be used alone, or two or more types of the basal mediums can be used in combination. A basal medium for constituting the serum-free medium "A" in one embodiment is preferably a medium in which an MCDB and a DMEM are mixed at a ratio of 1:1.

The serum-free medium "A" whose basal medium is added with an FGF, a PDGF, a TGF-β, an HGF, an EGF, at least one phospholipid, and at least one fatty acid may be used in the proliferation step of one embodiment. A content of the FGF in the basal medium is preferably 0.1 to 100 ng/ml at a final concentration, and more preferably 3 ng/ml. A content of the PDGF in the basal medium is preferably 0.5 to 100 ng/ml at a final concentration, and more preferably 10 ng/ml. A content of the TGF-β in the basal medium is preferably 0.5 to 100 ng/ml, and more preferably 10 ng/ml.

A content of the HGF in the basal medium is preferably 0.1 to 50 ng/ml at a final concentration, and more preferably ng/ml. A content of the EGF in the basal medium is preferably 0.5 to 200 ng/ml at a final concentration, and more preferably 20 ng/ml. A total content of phospholipid(s) in the basal medium is preferably 0.1 to 30 μg/ml at a final concentration, and more preferably 10 μg/ml. A total content of fatty acid(s) with respect to the basal medium is preferably 1/1000 to 1/10 of the basal medium, and more preferably 1/100.

The use of such serum-free medium "A" has the proliferation promoting effect, which is equal to or larger than that of a serum-containing medium, while preventing heteroprotein contamination. This makes it possible to desirably proliferate the mesenchymal stem cells.

In the proliferation step of the producing method according to the present invention, examples of a phospholipid contained in the serum-free medium "A" encompass phosohatidic acid, lysophosohatidic acid, phosphatidylinositol, phosphatidyl serine, phosphatidyl ethanolamine, phosphatidyl choline, and phosphatidyl glycerol. Those phospholipids can be used alone, or two or more types of the phospholipids can be used in combination. In one embodiment, the serum-free medium "A" may contain an phosohatidic acid and phosphatidyl choline in combination, and those phospholipids may be derived from animals or plants.

Examples of the fatty acids contained in the serum-free medium "A" encompass linoleic acid, oleic acid, linolenic acid, arachidonic acid, myristic acid, palmitoyl acid, palmitic acid, and stearic acid. The additive for a medium according to this embodiment may contain any one of those fatty acids alone or two or more types of the fatty acids in combination. Further, the serum-free medium "A" according to this embodiment may contain not only the fatty acid(s) but also cholesterol.

The term "FGF" used in the Specification means a growth factor selected from a fibroblast growth factor (FGF) family, and is preferably FGF-2 (bFGF). However, other FGFs of the FGF family, such as an FGF-1 etc., may be selected. The term "PDGF" used in the Specification means a growth factor selected from a platelet derived growth factor (PDGF) family, and is preferably a PDGF-BB or a PDGF-AB. The term "TGF-β" used in the Specification means a growth factor selected from a transforming growth factor-β (TGF-β) family, and is preferably TGF-β3. However, other TGF-βs of the TGF-β family may be selected.

The term "HGF" used in the Specification means a growth factor selected from a hepatocyte growth factor family, and the term "EGF" means a growth factor selected from an epidermal growth factor (EGF) family.

In one embodiment, the serum-free medium "A" may further contain at least two factors selected from the group consisting of a connective tissue growth factor (CTGF), a vascular endothelial growth factor (VEGF), and an ascorbic acid compound.

The term "ascorbic acid compound" used in the Specification means ascorbic acid (vitamin C), ascorbic acid-2-phosphoric acid, or a compound similar to those ascorbic acids.

Note that the growth factors contained in the serum-free medium "A" may be natural or may be produced by genetical modification.

In one aspect, the serum-free medium "A" preferably contains a lipid antioxidant. The lipid antioxidant contained in the serum-free medium "A" may be DL-α-tocopherol acetate (vitamin E) in one embodiment. The serum-free medium "A"

may further contain a surfactant. The surfactant contained in the serum-free medium "A" may be PLURONIC® F-68 or TWEEN® 80 in one embodiment.

The serum-free medium "A" may further contain insulin, transferrin, and selenate. The term "insulin" used in the Specification may be also an insulin-like growth factor and may be derived from a natural cell or may be genetically modified. The additive for a medium according to the present invention may further contain dexamethasone, or another glucocorticoid.

In the proliferation step, the mesenchymal stem cells isolated from an animal (such as humans) tissue or cell by a conventionally public-known method is inoculated on the serum-free medium "A" described above, and is cultured until the mesenchymal stem cells are proliferated to the desired number of cells. It is preferable that, as a culture condition: the mesenchymal stem cells (1 to $2\times10^4$) are inoculated in a medium (1 ml) and incubated at a culture temperature of 37° C.±1° C. for a culture time period in a range of 48 to 96 hours under 5% $CO_2$ environment. By culturing the mesenchymal stem cells as described above, it is possible to efficiently produce a large number of mesenchymal stem cells whose immunosuppression ability is maintained or improved.

In the proliferation step, a culture vessel for use in culturing is not particularly limited, provided that the mesenchymal stem cells can be proliferated. For example, a 75 $cm^2$ flask (FALCON®), a 75 $cm^2$ flask (manufactured by SUMITOMO BAKELITE CO., LTD.), etc. can be preferably used. Note, however, that proliferation of some cells are affected by kinds of culture vessels to be used. It is therefore preferable that, in order to proliferate more efficiently the mesenchymal stem cells, the mesenchymal stem cells to be proliferated (hereinafter, also referred to as a "proliferation target cell") in the proliferation step is subjected to the proliferation step by use of a culture vessel suitable for proliferation of these mesenchymal stem cells.

Examples of a method for selecting a culture vessel suitable for proliferation of a proliferation target cell encompass a method in which an optimum culture vessel is selected by the proliferation target cell. More specifically, multiple kinds of culture vessels are prepared, and proliferation target cells are proliferated under the same conditions other than the kinds of culture vessels. The number of cells in each vessel is measured by a public-known method on fourteenth day in culturing. It can be determined that a culture vessel having the largest number of cells is the most suitable for proliferating the proliferation target cell. Further, in a case where proliferation speed of the proliferation target cell is high, it can be determined that a culture vessel having a shortest period in which the proliferation target cells reach the number of cells of 80 to 90% of a confluent state is the most suitable for proliferating the proliferation target cell even if the culturing is carried out for less than two weeks.

In a case where a culture vessel suitable for the proliferation of the proliferation target cell has been already found out, the culture vessel may be used in the proliferation step of the producing method according to the present invention. On the contrary, in a case where a culture vessel suitable for proliferation of the proliferation target cell has not been found out yet, the producing method according to the present invention may further include, before the proliferation step, a "culture vessel selecting step" (described later) for selecting a culture vessel suitable for the proliferation of the proliferation target cell.

Note that adhesion of the mesenchymal stem cells to a culture vessel is a necessary condition for proliferating the mesenchymal stem cells. It is therefore preferable that, in a case where adhesion of the proliferation target cell to the culture vessel is not sufficient, the serum-free medium "A" further contains cell adhesion molecules in the proliferation step. Examples of the "cell adhesion molecules" encompass fibronectin, collagen, and gelatin. Those cell adhesion molecules can be used alone, or two or more types of the cell adhesion molecules can be used in combination.

Cell adhesion molecule content in the serum-free medium "A" is preferably 1 to 50 μg/ml at a final concentration, and more preferably 5 μg/ml at the final concentration. In one embodiment, where the cell adhesion molecules are fibronectin, fibronectin is added so that a final concentration of fibronectin in the serum-free medium "A" is 5 μg/ml. This can improve the adhesion efficiency of the proliferation target cell with respect to the culture vessel.

In the proliferation step, the mesenchymal stem cells may be subcultured at least once. The mesenchymal stem cells are proliferated anchorage-dependently. For example, in a case where the mesenchymal stem cells are locally unevenly proliferated, the culture condition of the mesenchymal stem cells can be improved by subculturing the mesenchymal stem cells in the middle of the proliferation step.

The subculturing of the mesenchymal stem cells may be carried out in any way, and may be performed by a conventionally public-known method of subculturing mesenchymal stem cells. For the sake of good cell conditions of the subcultured mesenchymal stem cells, it is preferable to peel off the mesenchymal stem cells by use of a cell remover which does not contain any component derived from mammal and microorganism in a case where the mesenchymal stem cells are to be subcultured in the proliferation step. Examples of the term "cell remover which does not contain any component derived from mammal and microorganism" encompass ACCUTASE™ cell remover (Innovative Cell Technologies, Inc.).

The following description will discuss an example of a subculturing method in a case where ACCUTASE™ cell remover is used as "the cell remover which does not contain any component derived from mammal and microorganism". The mesenchymal stem cells are peeled off by processes (i) to (vi), and is subcultured. Note that, in the following subculturing method, a T-25 flask FALCON® culture vessel is assumed to be used as a culture vessel.

(i) A cell layer is washed with PBS(−) (5 mL).
(ii) ACCUTASE™ cell remover (2 mL) is added.
(iii) The resultant liquid is let stand at a room temperature for about two minutes, and whether or not cells are released is checked. After that, a cell suspension fluid is moved to a tube.
(iv) PBS(−) (7 mL) is added into a culture vessel, so as to rinse a bottom surface of the flask with PBS (−).
(v) The resultant solution of the process (iv) is transferred to the tube of the process (iii), and is centrifuged at 1500 rpm (200×g) for five minutes.
(vi) Supernatant is removed, and the solution is inoculated to the serum-free medium "A" at inoculation density of 5,000 cells/$cm^2$.

Note that, in the proliferation step, it is preferable to provide mesenchymal stem cells which have been subcultured at least once (P1) after collection of mesenchymal stem cells from animal (such as human) tissues.

(Screening Step)

In a screening step (also referred to as a "first screening step") of the producing method according to the present invention, mesenchymal stem cells whose immunosuppression ability is maintained or improved is screened from the mesenchymal stem cells which have been subjected to the proliferation step. The mesenchymal stem cells proliferated in the serum-free medium "A" in the proliferation step at least maintain and even improve their immunosuppression ability. By screening such mesenchymal stem cells by use of the immunosuppression ability as a reference, it is possible to select mesenchymal stem cells whose immunosuppression ability is maintained or improved. The mesenchymal stem cells thus selected are used as a cell preparation. This makes it possible to realize a transplantation treatment of the mesenchymal stem cells in which immunorejection is down-regulated, without using an immunosuppressant.

The serum-free medium "A" does not contain heteroprotein, and can grow the mesenchymal stem cells without depriving the function as stem cells from the mesenchymal stem cells. Further, the mesenchymal stem cells cultured in the serum-free medium "A" have a proliferation ability higher than that of mesenchymal stem cells cultured in the bovine fetusserum-containing medium, and also has a high activity indicative of an immunosuppressive effect. In a case where mesenchymal stem cells cultured in the serum-free medium "A" is used for transplantation treatment, a cell having the function as a stem cell and the immunosuppression ability is increased and individual cells thus proliferated have high activity. It is therefore expected that the function and the immunosuppression ability create a synergistic effect.

Meanwhile, the inventors of the present invention discussed tumorigenicity conceivable from an effect of the proliferation ability of the serum-free medium "A" by testing by a soft agar culture method in vitro and a tumorigenicity test by use of high-sensitive immunodeficient mice (NOG mice) in vivo. Specifically, human mesenchymal stem cells derived from synovial membrane (3 lots) and human mesenchymal stem cells derived from bone marrow (1 lot) were cultured in the serum-free medium "A", and 1,000,000 of cultured cells were transplanted to a medium for a soft agar culture and ten subcutaneous parts of the NOG mice. As a result, in a case of the soft agar culture, a tumor colony was observed when 1,000 of Hela cells were transplanted, whereas in the test with the mesenchymal stem cells showed negative results (3 lots). Meanwhile, a tumor nodule was not observed in any transplanted tissues of the NOG mice under such experimental condition that a tumor nodule was detected even if only one Hep G2 cell was mixed in the NOG mice (data is not shown). From these reasons, it is clear that a cell preparation produced by the present invention is useful in transplantation treatment.

The term "immunosuppression ability" used in the Specification means ability to down-regulate immunorejection which occurs when a different kind or the same kind of cell etc. is xenotransplanted, and means ability to down-regulate an immune reaction by affecting functions of various immune effecter cells (e.g., by down-regulating proliferation of a T cell). This is a part of anti-inflammatory ability. The wording "the immunosuppression ability is maintained" used in the Specification means that the immunosuppression ability which mesenchymal stem cells naturally have is not lost by the proliferation step, and the wording "the immunosuppression ability is improved" means that the immunosuppression ability which mesenchymal stem cells have is improved after the proliferation step, as compared with the immunosuppression ability before the proliferation step is carried out.

In the screening step, the mesenchymal stem cells thus proliferated and an immune cell are co-cultured in the serum-free medium "A" which has been used in the proliferation step, and the number of immune cells in the medium is evaluated after the co-culturing is carried out. This makes it possible to screen the mesenchymal stem cells whose immunosuppression ability is maintained or improved, however, the present invention is not limited thereto. For example, as described in Example (described later), an increasing amount of the T cell or a production amount of cytokine is evaluated in a case where the T cell is used as the immune cell, and an increasing amount of a B cell or an activated NK cell is evaluated in a case where the B cell or the activated NK cell is used as the immune cell. This makes it possible to screen the mesenchymal stem cells whose immunosuppression ability is maintained or improved. Further, in a case where a dendritic cell is used as the immune cell, differentiation, maturation, activation, etc. of the dendritic cell are evaluated. This makes it possible to screen the mesenchymal stem cells whose immunosuppression ability is maintained or improved. The immune cell for use in such screening is preferably the T cell, the B cell, or the activated NK cell, and more preferably, the T cell or the B cell, and the most preferably the T cell.

(Second Screening Step)

The producing method according to the present invention may further include a second screening step in which mesenchymal stem cells which do not have the tumorigenicity are screened from the mesenchymal stem cells which has been subjected to the proliferation step.

The proliferation in the serum-free medium "A" in the proliferation step selectively grows the mesenchymal stem cells so that the number of the mesenchymal stem cells which do not have the tumorigenicity is increased. Such mesenchymal stem cells are screened by use of the tumorigenicity as a reference. This makes it possible to select a mesenchymal stem cells which do not have the tumorigenicity. Meanwhile, the mesenchymal stem cells thus selected are used as a cell preparation, and this realizes transplantation treatment of the mesenchymal stem cells which do not have the tumorigenicity. Therefore, the present invention also provides a method for producing a cell-preparation-containing mesenchymal stem cells which do not have the tumorigenicity under a serum-free condition.

Whether or not the mesenchymal stem cells have the tumorigenicity can be confirmed by a conventionally public-known method, such as the soft agar culture method in vitro or the tumorigenicity test by use of a high-sensitive immunodeficient mouse (NOG mouse) in vivo, as described in the "Screening step", however, the present invention is not limited to those methods. That is, the term "mesenchymal stem cells which do not have the tumorigenicity" used in the Specification means a mesenchymal stem cells which are confirmed that the mesenchymal stem cells do not have the tumorigenicity by the methods for confirming whether or not the mesenchymal stem cells have the tumorigenicity.

Note that, in a case where the producing method according to the present invention further includes the second screening step, an order in which the first screening step and the second screening step are carried out is not particularly limited. That is, the first screening step may be carried out before the second screening step, or alternatively, the first screening step may be carried out after the second screening step.

(Serum Culture Step)

The producing method according to the present invention further includes a serum culture step in which the mesenchymal stem cells which have been subjected to the proliferation step are cultured in a serum-containing medium before the screening step is carried out. In the serum culture step, the mesenchymal stem cells which have been cultured under a serum-free condition in the proliferation step are cultured in a serum-containing medium. In a case where the serum culture step is carried out, the mesenchymal stem cells are subjected to the screening step after being subjected to the serum culture step.

A conventionally public-known serum-containing medium can be used as the serum-containing medium for use in the serum culture step, such as a medium containing 10% FBS made by adding 10% FBS to the basal medium. In the serum culture step, the mesenchymal stem cells obtained in the proliferation step are inoculated and cultured in the serum-containing medium. It is preferable that, as a culture condition, (A) the number of mesenchymal stem cells are 1 to $2 \times 10^4$ with respect to a medium (1 ml), (B) the culture temperature is 37° C.±1° C., the culture time period is 48 to 96 hours, and (C) the mesenchymal stem cells are under 5% $CO_2$. By culturing the mesenchymal stem cells as described above, it is possible to efficiently and earlier obtain a larger number of the mesenchymal stem cells which have immunosuppression ability.

The mesenchymal stem cells cultured in the serum-containing medium are subjected to the screening step, and the mesenchymal stem cells whose immunosuppression ability is maintained or improved are selected.

As described above, the mesenchymal stem cells are pre-cultured in the serum-free medium "A", and are then cultured in the serum-containing medium. Therefore, the mesenchymal stem cells can obtain the immunosuppressive effect equal to or larger than that of mesenchymal stem cells which are pre-cultured and cultured in the serum-containing medium. Further, the mesenchymal stem cells exhibit the immunosuppressive effect earlier. Further, since serum is used only when the mesenchymal stem cells are cultured, the content of serum is low. This realizes low-serum culturing.

(Pre-Proliferation Step)

The producing method according to the present invention may further include, before the step (A), the step of: (D) pre-proliferating the mesenchymal stem cells in a serum-free medium B containing an FGF, a PDGF, an EGF, at least one phospholipid, and at least one fatty acid.

The term "serum-free medium B" is different from the serum-free medium "A" described in the "proliferation step" in that the serum-free medium B does not contain an HGF and TGF-β. Components other than the HGF and TGF-β (an FGF, a PDGF, an EGF, at least one phospholipid, and at least one fatty acid) and a basal medium are the same as those of the serum-free medium "A" described in the "proliferation step", so that the description thereof is herein omitted.

Further, in one aspect, the serum-free medium B preferably contains a lipid antioxidant, which is similar to the serum-free medium "A". Further, the serum-free medium B may further include a surfactant. Further, the serum-free medium B may further contain insulin, transferrin, and selenate. The serum-free medium B may further contain dexamethasone or another glucocorticoid. Those components also have already described in the serum-free medium "A" of the "proliferation step", so that the description thereof is herein omitted.

Note that contents of those components contained in the serum-free medium B may be the same as those of the serum-free medium "A" or may be different from those of the serum-free medium "A", provided that the contents of the components fall within ranges of the contents of the components of the serum-free medium "A" described in the "proliferation step".

In the pre-proliferation step, the mesenchymal stem cells isolated from an animal (such as human) tissue by a conventionally public-known method are inoculated in the serum-free medium B, and are cultured until the number of mesenchymal stem cells is proliferated to become the desired number of the mesenchymal stem cells. It is preferable that, as a culture condition, (A) tissue slices (containing MSCs) of 1 to 500 mg are separated with respect to a medium 1 ml, (B) the mesenchymal stem cells are inoculated, (C) the culture temperature is 37° C.±1° C., (D) a culture time period is 3 to 14 days, and (E) the mesenchymal stem cells are under the 5% $CO_2$.

The mesenchymal stem cells which are subjected to pre-proliferation step are not particularly limited. However, the mesenchymal stem cells are preferably initial mesenchymal stem cells, i.e., are preferably cells which have never been subcultured after being collected from an animal (such as human) tissue. As described in Examples (described later), initial mesenchymal stem cells are proliferated in advance in the serum-free medium B before the proliferation step is carried out. This makes it possible to remarkably proliferate the number of the mesenchymal stem cells in the proliferation step.

A method for culturing mesenchymal stem cells in the pre-proliferation step in one embodiment is, for example, as follows: the mesenchymal stem cells are inoculated in the serum-free medium B at inoculation density of $2 \times 10^5$ cells/$cm^2$; after that, the mesenchymal stem cells are incubated for about one week while the serum-free medium B is added therein every two days in an amount equivalent to 10% of the amount of the culture fluid at the inoculation until the number of cells reached 70 to 80% of a confluent state. The mesenchymal stem cells thus cultured in advance in the serum-free medium B are subjected to the proliferation step. This makes it possible to obtain a large number of mesenchymal stem cells whose immunosuppression ability is maintained or improved.

Further, in order to efficiently proliferate the mesenchymal stem cells in the pre-proliferation step, it is preferable that a pre-proliferation step is carried out with a culture vessel suitable for proliferation of the particular kind of the mesenchymal stem cells to be proliferated in the pre-proliferation step (hereinafter, these mesenchymal stem cells also referred to as a "pre-proliferation target cell"). A method for selecting a culture vessel suitable for pre-proliferation of the proliferation target cell has been described in the "proliferation step", so that the description thereof is herein omitted.

In a case where adhesion of the pre-proliferation target cell with respect to the culture vessel is not sufficient, the serum-free medium B may further contain cell adhesion molecules in the pre-proliferation step, which is similar to the proliferation step. The cell adhesion molecules have been described in the "proliferation step" so that the description thereof is herein omitted.

Mesenchymal stem cells may be subcultured at least once in the pre-proliferation step, which is similar to the proliferation step. It is possible to improve a culture condition by subculturing the mesenchymal stem cells in the middle of the pre-proliferation step. Note that it is preferable that the pre-proliferation step is preferably carried out during a period from primary cell culture (P0) to third cell culture (P3). A method for subculturing mesenchymal stem cells in the middle of the pre-proliferation step and a subculturing method to be carried out after the pre-proliferation step have been already described in the "proliferation step", so that the description thereof is herein omitted.

(Culture Vessel Selecting Step)

The producing method according to the present invention may further include, before the proliferation step (or before the pre-proliferation step), a culture vessel selecting step for selecting a culture vessel suitable for proliferation of the mesenchymal stem cells. The method for selecting a culture vessel suitable for proliferation of the mesenchymal stem cells has been described in the "proliferation step", so that the description thereof is herein omitted.

(2) Serum-Free Additive for a Medium for Producing a Cell Preparation

The present invention provides a serum-free additive for a medium for producing a cell preparation containing mesenchymal stem cells whose immunosuppression ability is maintained or improved. The additive for a medium according to the present invention contains an FGF, a PDGF, a TGF-β, an HGF, an EGF, at least one phospholipid, and at least one fatty acid. By adding the additive for a medium according to the present invention to a conventionally public-known basal medium, it is possible to use the conventionally public-known basal medium as a serum-free medium (serum-free medium "A") for producing the cell-preparation-containing mesenchymal stem cells whose immunosuppression ability is maintained or improved.

Examples of a phospholipid contained in an additive for a medium according to the present invention encompass phosohatidic acid, lysophosohatidic acid, phosphatidylinositol, phosphatidyl serine, phosphatidyl ethanolamine, phosphatidyl choline, and phosphatidyl glycerol. Those phospholipids can be used alone, or two or more types of the phospholipids can be used in combination. In one embodiment, the additive for a medium according to the present invention contains an phosphatidic acid and phosphatidyl choline in combination. Further, those phospholipids may be derived from animals or plants.

Examples of the fatty acids contained in the additive for a medium according to this embodiment encompass linoleic acid, oleic acid, linolenic acid, arachidonic acid, myristic acid, palmitoyl acid, palmitic acid, and stearic acid. The additive for a medium according to this embodiment may contain any one of those fatty acids alone or two or more types of the fatty acids in combination. Further, the additive for a medium according to this embodiment may contain not only the fatty acid(s) but also cholesterol.

The term "FGF" used in the Specification means a growth factor selected from a fibroblast growth factor (FGF) family, and is preferably FGF-2 (bFGF). However, other FGFs of the FGF family, such as an FGF-1 etc., may be selected. The term "PDGF" used in the Specification means a growth factor selected from a platelet derived growth factor (PDGF) family, and is preferably a PDGF-BB or a PDGF-AB. The term "TGF-β" used in the Specification means a growth factor selected from a transforming growth factor-β (TGF-β) family, and is preferably TGF-β3. However, other TGF-βs of the TGF-β family may be selected.

The term "HGF" used in the Specification means a growth factor selected from a hepatocyte growth factor family, and the term "EGF" means a growth factor selected from an epidermal growth factor (EGF) family.

In one embodiment, the serum-free medium "A" may further contain at least two factors selected from the group consisting of a connective tissue growth factor (CTGF), a vascular endothelial growth factor (VEGF), and an ascorbic acid compound.

The term "ascorbic acid compound" used in the Specification means ascorbic acid (vitamin C), ascorbic acid-2-phosphoric acid, or a compound similar to those ascorbic acids.

Note that growth factors contained in the additive for a medium according to the present invention may be natural or may be produced by genetical modification.

In one aspect, the additive for a medium according to the present invention preferably contains a lipid antioxidant. The lipid antioxidant contained in the additive for a medium according to this embodiment may be DL-α-tocopherol acetate (vitamin E) in one embodiment. The additive for a medium according to the present invention may further contain a surfactant. The surfactant contained in the additive for a medium according to this embodiment may be PLURONIC® F-68 or TWEEN® 80 in one embodiment.

The additive for a medium according to the present invention may further contain insulin, transferrin, and selenate. The term "insulin" used in the Specification may be also an insulin-like growth factor and may be derived from a natural cell or may be genetically modified. The additive for a medium according to the present invention may further contain dexamethasone, or another glucocorticoid.

(3) Kit for Carrying Out Serum-Free Culturing with Respect to Animal Cell

The present invention provides the serum-free additive for a medium for producing a cell preparation containing a mesenchymal stem cells whose immunosuppression ability is maintained or improved. The additive for a medium (additive "A" for the medium) according to the present invention contains an FGF, a PDGF, a TGF-β, an HGF, an EGF, at least one phospholipid, and at least one fatty acid. The additive for a medium according to the present invention may further include cell adhesion molecules.

A kit for the additive for a medium according to the present invention may contain an FGF, a PDGF, a TGF-β, an HGF, an EGF, at least one phospholipid, and at least one fatty acid in one vessel, or separately contain those components. The kit for the additive for a medium according to the present invention may further contain cell adhesion molecules.

The cell adhesion molecules have been described in the "proliferation step" of "(1) Method for Producing Cell Preparation Containing Mesenchymal Stem Cells" in the Specification, so that the description thereof is herein omitted.

By using the kit for the additive for a medium according to the present invention to a conventionally public-known basal medium, it is possible to add the additive to the conventionally public-known basal medium, thereby preparing a serum-free medium (serum-free medium "A") for producing a cell preparation containing mesenchymal stem cells whose immunosuppression ability is maintained or improved.

In the Specification, the term "composition" means a composition in which various main components are contained in one material, and the term "kit" means a kit in which at least one of the various main components is contained in a material other than one material in which the rest of the various main components is contained. Therefore, it is easily understood that the growth factors, the at least one phospholipid, and the at least one fatty acid included in the kit for the additive for a medium according to the present invention are the same as those described in the additive for a medium.

The kit according to the present invention is a kit for producing a cell preparation containing mesenchymal stem cells whose immunosuppression ability is maintained or improved, and includes at least the additive for a medium (additive "A" for a medium) according to the present invention. Further, the kit according to the present invention may further include the additive B for the medium containing an FGF, a PDGF, an EGF, at least one phospholipid, and at least one fatty acid. Note that the description of the "serum-free medium B" can be also read as the description for the "additive B for the medium".

(4) Serum-Free Culturing Medium for Producing Cell Preparation

The present invention provides a serum-free culturing medium for producing a cell preparation containing mesenchymal stem cells whose immunosuppression ability is maintained or improved. A culturing medium according to the present invention contains an FGF, a PDGF, a TGF-β, an HGF, an EGF, at least one phospholipid, and at least one fatty acid. The culturing medium according to the present invention can be used as a serum-free medium (serum-free medium "A") for producing a cell preparation containing mesenchymal stem cells whose immunosuppression ability is maintained or improved.

The culturing medium according to the present invention contains an FGF, a PDGF, a TGF-β, an HGF, an EGF, at least one phospholipid, and at least one fatty acid, and those components may be simultaneously added to the basal medium, or may be separately added. That is, it can be said that the culturing medium according to the present invention only needs to contain the components contained in the additive for a medium or the components contained in the kit for the additive for a medium.

The basal medium for constituting the culturing medium according to the present invention is not particularly limited, provided that the basal medium is a basal medium for animal cells, which is well-known in this field is medium, and examples of preferable basal media encompass a Ham's F12 medium, a DMEM medium, an RPMI-1640 medium, and an MCDB medium. Those basal media can be used alone, or two or more types of the basal media can be used in combination. In one embodiment, a medium in which an MCDB and a DMEM are mixed at a ratio of 1:1 is preferable as the basal medium for constituting the culturing medium according to the present invention.

(5) Culture Method for Producing Cell Preparation

The present invention provides a culture method for producing a cell preparation containing mesenchymal stem cells whose immunosuppression ability is maintained or improved. The culture method according to the present invention includes a step (culture step "A") in which the mesenchymal stem cells are cultured in the serum-free medium (serum-free medium "A") containing an FGF, a PDGF, a TGF-β, an HGF, an EGF, at least one phospholipid, and at least one fatty acid. In the culture method according to the present invention, the serum-free culturing medium can be used in order to culture the mesenchymal stem cells.

The culture method according to the present invention may further include, before the culture step "A", a step for culturing mesenchymal stem cells (culture step B) in the serum-free medium B containing an FGF, a PDGF, an EGF, at least one phospholipid, and at least one fatty acid.

Note that the "culture step A" and the "culture step B" correspond to the "proliferation step" and the "pre-proliferation step", respectively, in the method for producing a cell preparation containing mesenchymal stem cells according to the present invention. Accordingly, the description of the "proliferation step" and the "pre-proliferation step" in "(1) Method for Producing Cell Preparation Containing Mesenchymal Stem Cells" in the Specification can be also read as the descriptions of the "culture step A" and "culture step B", respectively.

In one embodiment, the culture method according to the present invention may include a step for simultaneously adding an FGF, a PDGF, a TGF-β, an HGF, an EGF, at least one phospholipid, and at least one fatty acid to the basal medium. In one embodiment, the culture method according to the present invention may include a step for adding, to the basal medium, an FGF, a PDGF, an EGF, at least one phospholipid, and at least one fatty acid at once. The basal medium is not particularly limited, provided that the basal medium is a medium for animal cells, which is well-known in this field.

(6) Further Usage

According to the present invention as described above, it is possible to proliferate, even in the serum-free or a low-serum medium, the mesenchymal stem cells at a speed equal to or higher than that obtained in a case where the mesenchymal stem cells are cultured in the serum-containing medium, and immunosuppression ability of the mesenchymal stem cells thus proliferated are maintained or improved. Further, the mesenchymal stem cell proliferated in the present invention which do not have the tumorigenicity are selectively increased. Differentiation ability of the mesenchymal stem cells proliferated in the present invention (see Patent Literature 1). Accordingly, when a cell preparation containing such mesenchymal stem cells is administered to a patient, it is possible not only to realize a great transplantation treatment because of the mesenchymal stem cells, but also to effectively suppress immunorejection which is a large problem for the transplantation treatment. This makes it possible to reduce the burden on a patient and realize a stable treatment. It is unnecessary to consider a lot difference of the serum, as compared with a conventional cell preparation produced by use of the serum. This makes it possible to realize a stable cure rate in the transplantation treatment.

It can be said that the mesenchymal stem cells contained in the cell preparation produced by the present invention maintain a function of affecting an immune effecter cell, which function the mesenchymal stem cells originally have. The mesenchymal stem cells have an immunoregulation effect and an immune tolerance effect, so that it can be expected that the cell preparation produced by the present invention is used for treatments to exhibit those effects. Further, it can be also expected that the mesenchymal stem cells according to the cell preparation produced by the present invention also serves as a function of the anti-inflammatory effect of the mesenchymal stem cells in transplantation treatment. Further, the cell preparation is expected to exhibit an anti-aging effect by exhibiting the anti-inflammatory effect of the mesenchymal stem cells.

The cell preparation produced by the present invention can be used for treatment for a local disease, in which treatment the mesenchymal stem cells are administered (locally administered) to a site which needs transplantation of the mesenchymal stem cells. In addition, by administering the mesenchymal stem cells to a whole body, i.e., by administering the mesenchymal stem cells into a vein etc. and conveying the mesenchymal stem cells to a whole body, it is possible to treat strong immunorejection more effectively because of an acute GVHD etc. caused by bone marrow transplantation etc. It is therefore expected to remarkably improve a survival rate of humans. Further, a cell preparation produced by the present invention is a cell preparation produced by serum-free culture. Accordingly, a useful growth factor or a differentiation factor is not nonspecifically adsorbed together with a serum protein to a transplantation material such as ceramics etc. Accordingly, a tissue-regenerative power caused by the transplantation of the cell preparation produced by the present invention is greatly high. This leads a high therapeutic effect. It is needless to say that it is possible to perform treatment in which both local administration and whole-body administration are performed in combination.

The immunosuppression ability of the mesenchymal stem cells contained in the cell preparation produced by the present invention is maintained or improved, and the mesenchymal stem cells suppress immunorejection caused when transplantation is performed. It is therefore possible to use the mesenchymal stem cells for treatment in which a non-self tissue or cell is transplanted (xenotransplantation) to another person (a donor and a recipient are different). The mesenchymal stem cells can be also preferably used not only for allotransplantation (allogeneic transplantation) by use of a human tissue or a human cell but also for xenotransplantation (heterotransplantation) by use of an animal (other than human) tissue or an animal (other than human) cell.

The cell preparation produced by the present invention exhibits the immunosuppressive effect earlier than a conventional mesenchymal stem cells produced by use of only a serum-containing medium, so that the cell preparation of the present invention is desired to early exhibit a therapeutic effect in a case where transplantation is performed. It is therefore expected that the cell preparation of the present invention increases the cure rate.

The method for producing the cell preparation containing mesenchymal stem cells according to the present invention, may further include, before the step (B), the step of: (C) culturing, in a medium containing serum, the mesenchymal stem cells which have been subjected to the step (A).

It is preferable that the method for producing the cell preparation containing mesenchymal stem cells further includes, before the step (A), the step of: (D) pre-proliferating the mesenchymal stem cells in a serum-free medium B containing an FGF, a PDGF, an EGF, at least one phospholipid, and at least one fatty acid.

The method may further include the step of: (E) screening the mesenchymal stem cells which do not have tumorigenicity, from the mesenchymal stem cells proliferated in the step (A).

In the method for producing the cell preparation containing mesenchymal stem cells according to the present invention, it is preferable that, in the step (A), the mesenchymal stem cells are proliferated by use of a culture vessel suitable for proliferation of the mesenchymal stem cells In the method for producing a cell preparation containing mesenchymal stem cells according to the present invention, it is preferable that the serum-free medium "A" further contains cell adhesion molecules in the step (A).

In the method for producing the cell preparation containing mesenchymal stem cells according to the present invention, the mesenchymal stem cells may be subcultured at least once in the step (A).

In the method for producing the cell preparation containing mesenchymal stem cells according to the present invention, it is preferable that, in the step (A), the subculturing is performed in such a way that the mesenchymal stem cells are peeled off by use of a cell removing agent which does not contain a component derived from a mammal or a microorganism.

The method for producing the cell preparation containing mesenchymal stem cells according to the present invention, may further include, before the step (A), the step of: selecting the culture vessel suitable for the proliferation of the mesenchymal stem cells.

In the method for producing the cell preparation containing mesenchymal stem cells according to the present invention, the phospholipid is selected from the group consisting of phosohatidic acid, lysophosohatidic acid, phosphatidylinositol, phosphatidyl serine, phosphatidyl ethanolamine, phosphatidyl choline, and phosphatidyl glycerol.

In the method for producing the cell preparation containing mesenchymal stem cells according to the present invention, the fatty acid is selected from the group consisting of linoleic acid, oleic acid, linolenic acid, arachidonic acid, myristic acid, palmitoyl acid, palmitic acid, and stearic acid.

An additive for a medium according to the present invention may further include cell adhesion molecules.

A kit according to the present invention, further include an additive B for a medium containing an FGF, a PDGF, an EGF, at least one phospholipid, and at least one fatty acid.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

All the professional literatures and Patent Literature described in the Specification are quoted as reference in the Specification.

EXAMPLES

Hereinafter, the present invention will be specifically described with reference to Examples, however, the present invention is not limited by the Examples.

Example 1

The following experiment was carried out.
(1. Cell Culture)
Mesenchymal stem cells derived from a human bone marrow (bone-marrow derived hMSCs) were bought from Lonza Walkersville, Inc. (hereinafter, Lonza Inc.), and the mesenchymal stem cells were cultured in Mesenchymal Stem Cell Basal Medium (MSCBM) (Lonza Inc.) added with Mesenchymal Cell Growth Supplement (MCGS) (Lonza Inc.), a serum-containing medium (MSCGM medium) or in a serum-free medium 1 shown in Table 1.

TABLE 1

| | Source | Effective concentration | Optimum concentration |
|---|---|---|---|
| Basal medium | | | |
| DMEM/MCDB201 | SIGMA ®: D6046/M6770 | 1:1 | |
| Supplement A (Basic factor) | | | |
| (human recombinant) Basic fibroblast growth factor (bFGF) | PEPROTECH ®: 100-18B | 0.1~100 ng/ml | 3 ng/ml |
| Dexamethasone (Dex) | SIGMA ®: D1756 | $10^{-6}$~$10^{-10}$M | $10^{-8}$M |
| (human recombinant) Insulin | Wako: 090-03446 | 0.5~50 µg/ml | 6.25 µg/ml |
| Transferrin | SIGMA ®: T0665 | 0.5~50 µg/ml | 6.25 µg/ml |
| Selenous acid | SIGMA ®: 21,117-6 | 0.1~50 ng/ml | 6.25 ng/ml |
| Bovine serum albumin0020(BSA) | SIGMA ®: A8806 | 0.1~50 mg/ml | 1.25 mg/ml |
| Supplement B-1 (Basic lipid 1) | | | |
| Chemically defined lipid concentrate (CD) | GIBCO ®: 11905-031 | 1/1000~1/10 | 1/100 |

TABLE 1-continued

| Source | Effective concentration | Optimum concentration |
|---|---|---|
| Supplement B-2 (Basic lipid 2) | | |
| Lecithin from Soybean (LS)  Waco: 120-00832 | 0.5~50 µg/ml | 10 µg/ml |
| cholesterol lipid concentrate (chol)  GIBCO ®: 12531-018 | 0.1~30 µg/ml | 3 µg/ml |
| (+α)-Tocopherol-Acetate (VE)  SIGMA ®: T1157 | 0.1~50 µg/ml | 2 µg/ml |
| Supplement C | | |
| (human recombinant) Hepatocyte growth factor (HGF)  SIGMA ®: H1404 | 0.1~50 ng/ml | 5 ng/ml |
| (human recombinant) Transforming growth factor-β$_3$ (TGF-β$_3$)  PEPROTECH ®: 100-36 | 0.5~100 ng/ml | 10 ng/ml |
| (human recombinant) Platelet derived growth factor (PDGF-BB)  Waco: 160-19741 | 0.5~100 ng/ml | 10 ng/ml |
| Others | | |
| (human recombinant) Epidermal growth factor (EGF)  Waco: 050-07141 | 0.5~200 ng/ml | 20 ng/ml |
| Ascorbic acid (VC)  SIGMA ®: A8960 | 0.5~200 µg/ml | 50 µg/ml |
| Phosphatidylcholine (PC)  Wako: 163-21181 | 0.5~100 µg/ml | 10 µg/ml |
| Phosphatidic acid sodium salt (PA)  SIGMA ®: P9511 | 0.5~100 µg/ml | 10 µg/ml |
| (human recombinant) Vascular Endothelial Growth Factor (VEGF)  SIGMA ®: V3388 | 0.5~100 ng/ml | 10 ng/ml |
| (human recombinant) Connective Tissue Growth Factor (CTGF)  Wako: 036-19471 | 0.1~20 µg/ml | 1 µg/ml |

(Concentration of undiluted solution: Arachidonic Acid 2.0 µg/ml, Cholesterol 220.00 µg/ml, DL-α-Tocopherol-Acetate 70.00 µg/ml, Linoleic Acid 540.00 µg/ml, Linolenic Acid 10.00 µg/ml, Myristic Acid 10.00 µg/ml, Oleic Acid 10.00 µg/ml, Palmitoleic Acid 10.0 µg/ml, Palmitic Acid 10.0 µg/ml, Stearic Acid 10.00 µg/ml)

A spleen BALB/c (H-2d) as a mouse splenocyte bought from CHARLES RIVER LABORATORIES JAPAN, INC. was ground and hemolized, then was suspended in 1% FBS/Advanced PRM1 (GIBCO®) was used in an experiment.

(2. Activation of Spleen Cell)

<2-1: Stimulation by Mitogen>

Mouse spleen cells ($1 \times 10^5$) were inoculated on each well of a 96-well-plate, and stimulated by Phorbol 12-myristate 13-acetate (hereinafter, referred to as "PMA") (2.5 ng/ml) and ionomycin (125 ng/ml).

<2-2: Stimulation by anti-CD3/anti-CD28>

The mouse spleen cells ($1 \times 10^5$) were inoculated on each well of the 96-well-plate, and were stimulated by anti-CD3 (2.5 g/ml) and anti-CD28 (0.5 µg/ml).

(3. Co-Culture of Activated Spleen Cell and hMSC Derived From Bone Marrow)

As a pre-process of bone-marrow derived hMSCs, the bone-marrow derived hMSCs ($1 \times 10^4$) is inoculated on each well of the 96-well-plate, and adhesion of the hMSCs to each well was confirmed (by the culture during several hours or overnight), and after that, the hMSCs were irradiated with gamma irradiation by use of a gamma cell 40 exactor. This inhibits cell division of the hMSCs. Then, the mouse spleen cells activated as described above were inoculated on each well to which the hMSCs were adhered, and then co-cultured with the bone-marrow derived hMSCs.

(4. Cell Proliferation Measurement)

[$^3$H]-Thymidine was added to each well on the third day or the fourth day in the co-culturing system, and the cells including hMSCs in the wells were cultured for another 8 hours. The cultured cells were adsorbed to a glass filter, and Thymidine intake was measured by a liquid scintillation counter, thereby measuring proliferation of the cells.

(5. Results)

Results of the co-culture of the hMSC derived from bone marrow and the activated mouse T cell in the MSCGM medium containing 10% FBS or in the medium 1 (STK2 (registered trademark)) which is a serum-free medium "A", are shown in FIGS. 1 to 4. In FIGS. 1 to 4, each value is shown by average±standard deviation. Similar results can be obtained from results of independent experiments which were carried out three or more times. #4 and #5 show respective results of hMSCs derived from bone marrow of two different individuals.

Figure 2:
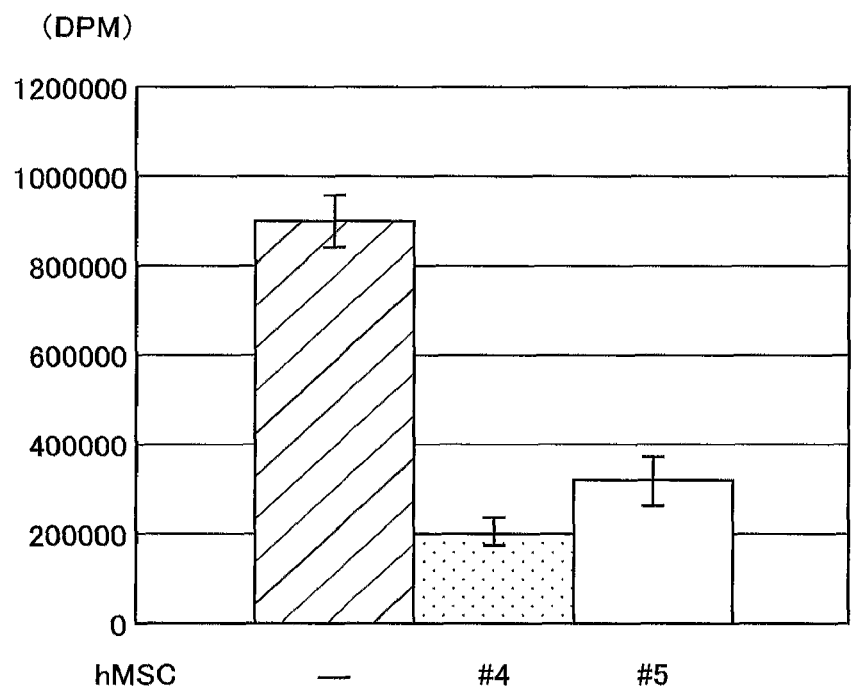
FIG. 2 is a graph showing an immunosuppressive effect of hMSCs on anti-CD3 and anti-CD28 stimulation T cell proliferative responses in a case where activated mouse T cells and an hMSC were co-cultured in a serum-free medium "A" according to one embodiment of the present invention.

FIG. 1 is a graph showing an immunosuppressive effect of bone-marrow derived hMSCs on anti-CD3 and anti-CD28 stimulation T cell proliferative responses in a case where activated mouse T cells and bone-marrow derived hMSCs are co-cultured in the MSCGM medium. FIG. 2 is a graph showing the immunosuppressive effect of bone-marrow derived hMSCs on anti-CD3 and anti-CD28 stimulation T cell proliferative responses in a case where activated mouse T cells and bone-marrow derived hMSCs are co-cultured in the medium 1.

Figure 3:
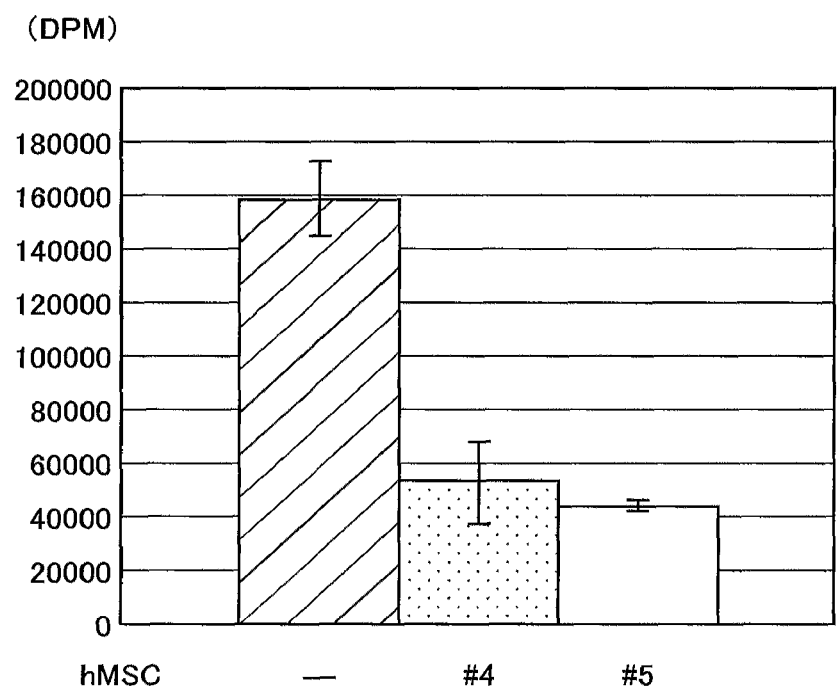
FIG. 3 is a graph showing an immunosuppressive effect of hMSCs on a mitogen stimulation T cell proliferative response in a case where activated mouse T cells and the hMSCs were co-cultured in an MSCGM medium.
Figure 4:
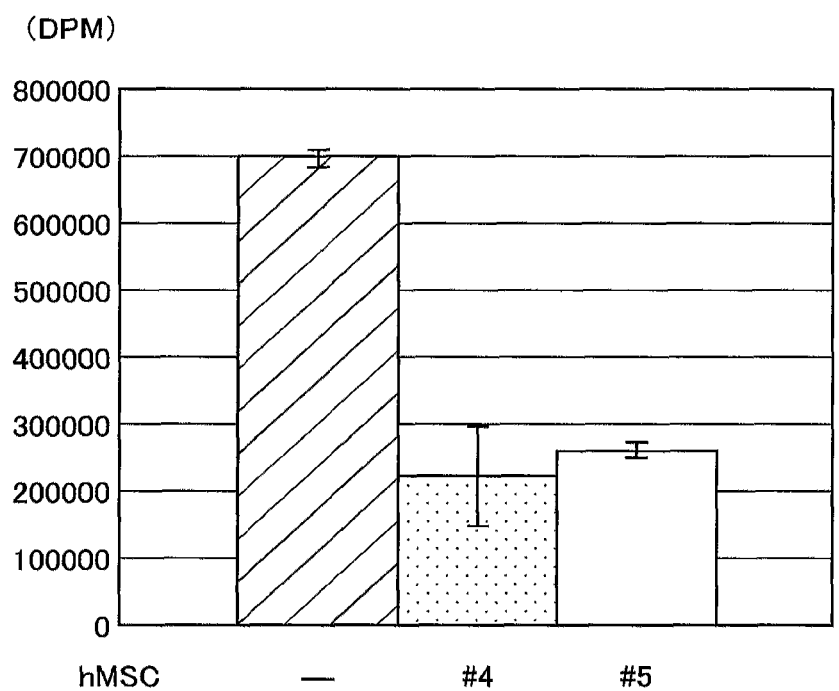
FIG. 4 is a graph showing an immunosuppressive effect of hMSCs on a mitogen stimulation T cell proliferative response in a case where activated mouse T cells and the hMSCs were co-cultured in a serum-free medium "A" according to one embodiment of the present invention.

FIG. 3 is a graph showing an immunosuppressive effect of hMSCs derived from bone marrow on PMA and ionomycin stimulation (mitogen stimulation) T cell proliferation reactions in a case where activated mouse T cells and bone-marrow derived hMSCs were co-cultured in the MSCGM medium. FIG. 4 is a graph showing the immunosuppressive effect of bone-marrow derived hMSCs on the PMA and ionomycin stimulation (mitogen stimulation) T cell proliferation reactions in a case where activated mouse T cells and bone-marrow derived hMSCs were co-cultured in the medium 1.

As shown in FIGS. 1 to 4, the bone-marrow derived hMSCs in the medium 1 suppressed proliferation of the T cells activated by the mitogen stimulation and proliferation of the T cells activated by the anti-CD3/anti-CD28 stimulation, which is similar to the bone-marrow derived hMSCs in the MSCGM medium containing serum. That is, FIGS. 1 to 4 show that the bone-marrow derived hMSCs, which were cultured by use of the serum-free medium 1, maintained an immunosuppression effect.

Example 2

An immunosuppressive effect of bone-marrow derived hMSCs on T cell proliferation caused by a mouse mixed lymphocyte reaction (MLR) was tested. An experiment method and cells and mediums used in this experiment are the same as those of Example 1. The hMSCs ($2\times10^4$) derived from bone marrow were inoculated on each well of a 96-well-plate as a pre-process of the bone-marrow derived hMSCs, and Example 2 was carried out in the same way as Example 1. Mouse spleen cells were activated by co-culturing mouse spleen cells ($2\times10^5$) and dendritic cells (BMDCs) derived from mouse bone marrow ($3.3\times10^4$) in each well of the 96-well-plate (MLR stimulation).

Note that the BMDCs for use in the experiment were cells which were inhibited from dividing, and those cells were prepared by: collecting and hemolysizing bone marrow cells from C3H (H-2k) bought from CHARLES RIVER LABORATORIES JAPAN, INC.; culturing the bone marrow cells with a medium changed on alternate days, where the medium was 1% FBS/Advanced PRMI (GIBCO®) containing a GM-CSF; stimulating the bone marrow cells by use of LPS (100 ng/ml) on the sixth day in this culturing; culturing the bone marrow cells over night; then washing the bone marrow cells; and irradiating the bone marrow cells with gamma rays by use of a gamma cell 40 exactor.

Figure 5:
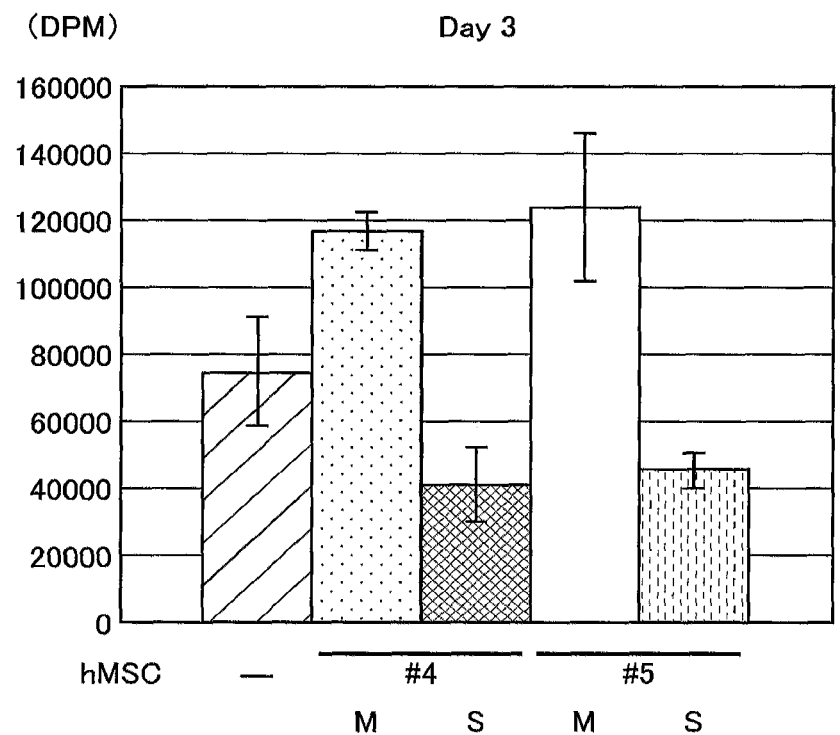
FIG. 5 is a graph showing an immunosuppressive effect of hMSCs on a mouse mixed lymphocyte reaction stimulation T cell proliferative response (results of the third day in culturing).
Figure 6:
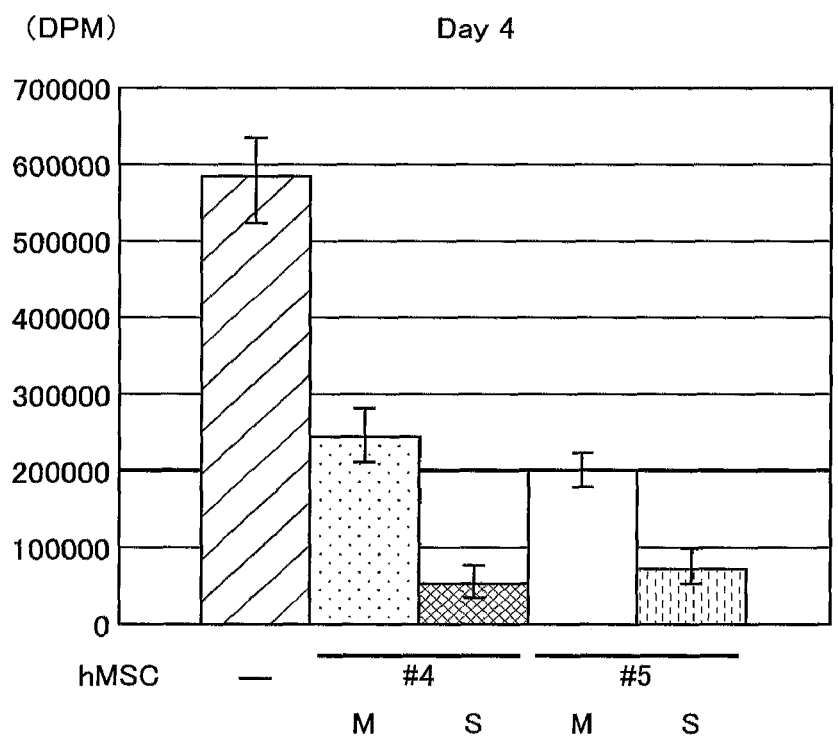
FIG. 6 is a graph showing an immunosuppressive effect of hMSCs on a mouse mixed lymphocyte reaction stimulation T cell proliferative response (results of the fourth day in culturing).

The bone-marrow derived hMSCs were pre-cultured in the MSCGM medium and the medium 1, and then the bone-marrow derived hMSCs subjected to this pre-culturing were co-cultured, in the MSCGM medium, with the mouse spleen cells activated as described above. Results of the experiment are shown in FIGS. 5 and 6. FIGS. 5 and 6 are graphs each showing the immunosuppressive effect of bone-marrow derived hMSCs on the T cell proliferation caused by the MLR. Each value is shown by average±standard deviation. Similar results can be obtained from results of independent experiments which were carried out three or more times. FIG. 5 shows results of the third day in the culturing, and FIG. 6 shows results of the fourth day in the culturing. In the drawings, the letter "M" shows results of a case where the hMSCs were pre-cultured in the MSCGM medium and cultured in the serum-containing medium, and the letter "S" shows results of a case where the hMSCs were pre-cultured in the medium 1 and were cultured in the serum-containing medium.

As shown in FIGS. 5 and 6, the bone-marrow derived hMSCs, pre-cultured in the medium 1, maintained an activated T cell proliferation suppression effect like the bone-marrow derived hMSCs pre-cultured in the MSCGM medium. The bone-marrow derived hMSCs pre-cultured in the MSCGM medium showed the immunosuppressive effect on the fourth days of the co-culturing, meanwhile, the bone-marrow derived hMSCs pre-cultured in the medium 1 already showed the immunosuppressive effect on the third day in the co-culturing. That is, the bone-marrow derived hMSCs pre-cultured in the medium 1 showed the immunosuppressive effect earlier. Further, although data were not shown, the bone-marrow derived hMSCs pre-cultured in the medium 1 showed similar results with respect to the mitogen stimulation T cell proliferation and the anti-CD3/anti-CD28 stimulation T cell proliferation.

It was confirmed that, as shown in the results of Examples 1 and 2, the bone-marrow derived hMSCs cultured in the medium 1 not only maintained the activated T cell proliferation suppression effect, but also exhibited the activated T cell proliferation suppression effect earlier than the bone-marrow derived hMSCs cultured in the MSCGM medium (serum-containing medium) did. Further, in a case where the bone-marrow derived hMSCs pre-cultured in the MSCGM medium and the activated mouse spleen cells were co-cultured, the T cells before the bone-marrow derived hMSCs showed the immunosuppressive effect are proliferated more actively than those in a control medium (which is a culturing medium of the activated mouse spleen cells, which culturing medium does not contain the bone-marrow derived hMSCs).

The experiment showed that, in a case where the bone-marrow derived hMSCs were cultured in the medium 1 as described above, the hMSCs not only had the advantage of proliferating the necessary number of cells in a short period, but also maintained the immunosuppressive effect. For this reason, it can be said that the medium 1 is effective at culturing the bone-marrow derived hMSCs especially for the purpose of clinical application.

Example 3

Figure 7:
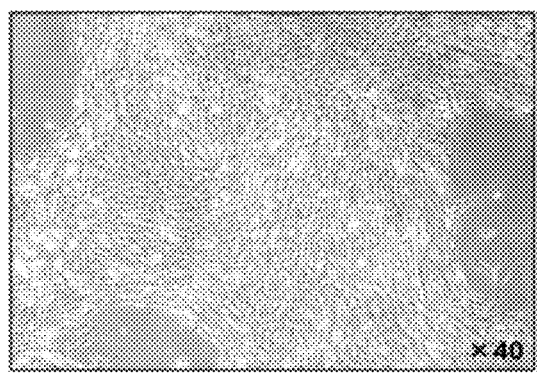
FIG. 7 is views each illustrating a proliferated state of hMSCs derived from adipose tissues on the eighth day in culturing.
Figure 7:
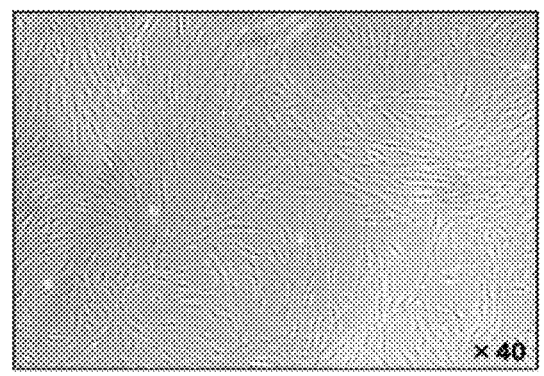

The following experiment was carried out.
(1. Cell Culture)
Mesenchymal stem cells derived from human adipose tissues (adipose tissue derived hMSCs) were separated and cultured in the following processes (i) to (vii).
(i) Adipose tissues were collected from a human, and were washed twice or three times with a serum-free DMEM medium.
(ii) The adipose tissues thus washed were cut into small pieces by use of scissors (1 mm$^3$).
(iii) The adipose tissues were treated with the use of a 0.1~0.2% collagenase (GIBCO® 17100-017) solution under agitation by a stirrer bar (37° C., 30-60 minutes).
(iv) The adipose tissues subjected to the collagenase process were filtered via a filter (100 mm), and were centrifuged (100×g) for 10 minutes. Thereby, hMSCs derived from the adipose tissues were separated from the adipose tissues.
(v) The centrifuged cells were treated with a Red lysis buffer (SIGMA® R7757) under agitation by a stirrer bar (for 5~10 minutes).
(vi) The cells subjected to the Red lysis buffer process were washed twice or three times with a serum-free DMEM medium.
(vii) The cells thus washed were inoculated on a culture plate (BECTON, DICKINSON FALCON® culture plate 353047), and were cultured in the serum-free medium 1 shown in Table 1, or in an MEM medium containing 10% FBS (SIGMA® D6046) (referred to as a "10% FBS-MEM").
(2. Cell Proliferation Measurement)
A proliferated state of the cells was visually observed by use of an optical microscope on the eighth day in the culturing.
(3. Result)
Results were shown in FIG. 7. FIG. 7 is views each illustrating a proliferated state of hMSCs derived from adipose tissues on the eighth day in the culturing. In FIG. 7, the hMSCs derived from the adipose tissues were observed with a magnification of forty times. It was shown that, as shown in FIG. 7, the number of the hMSCs derived from the adipose tissues cultured in the medium 1 was remarkably increased in comparison with the number of the hMSCs derived from the adipose tissues cultured in the 10% FBS-MEM (the hMSCs in the medium 1 were twice to three times as many as those in the 10% FBS-MEM).

Example 4

The following experiment was carried out.
(1. Cell Culture)
Mesenchymal stem cells derived from a human synovial membrane (synovial membrane derived hMSCs) were separated in the following processes (i) to (iii).

(i) A synovial membrane was collected from a human.
(ii) Cells of the synovial membrane thus collected were washed with PBS, tissues were added into and mixed with a 0.4% collagenase solution (10 ml), and were reacted at 37° C. for 1 to 4 hours.
(iii) The reacted mixture was filtered and centrifuged.

Initial synovial membrane derived hMSCs obtained by centrifugation were cultured with the following media. Note that a medium 2 which is a serum-free medium B is a medium obtained by removing an HGF and a TGF-β from the medium 1 shown in Table 1.

10% FBS containing DMEM (10% FBS-DMEM) (SIGMA® D6046, FBS; HYCLONE®, PS(+).
  medium 1
  medium 2

The initial synovial membrane derived hMSCs were cultured in a carbon dioxide incubator (95% air and 5% $CO_2$) at 37° C.

(2. Cell Proliferation Measurement)
A proliferated state of those cells was visually observed by use of an optical microscope on the twelfth day in culturing (no subculturing). Further, the number of cells were counted by a coulter counter.

Figure 8:
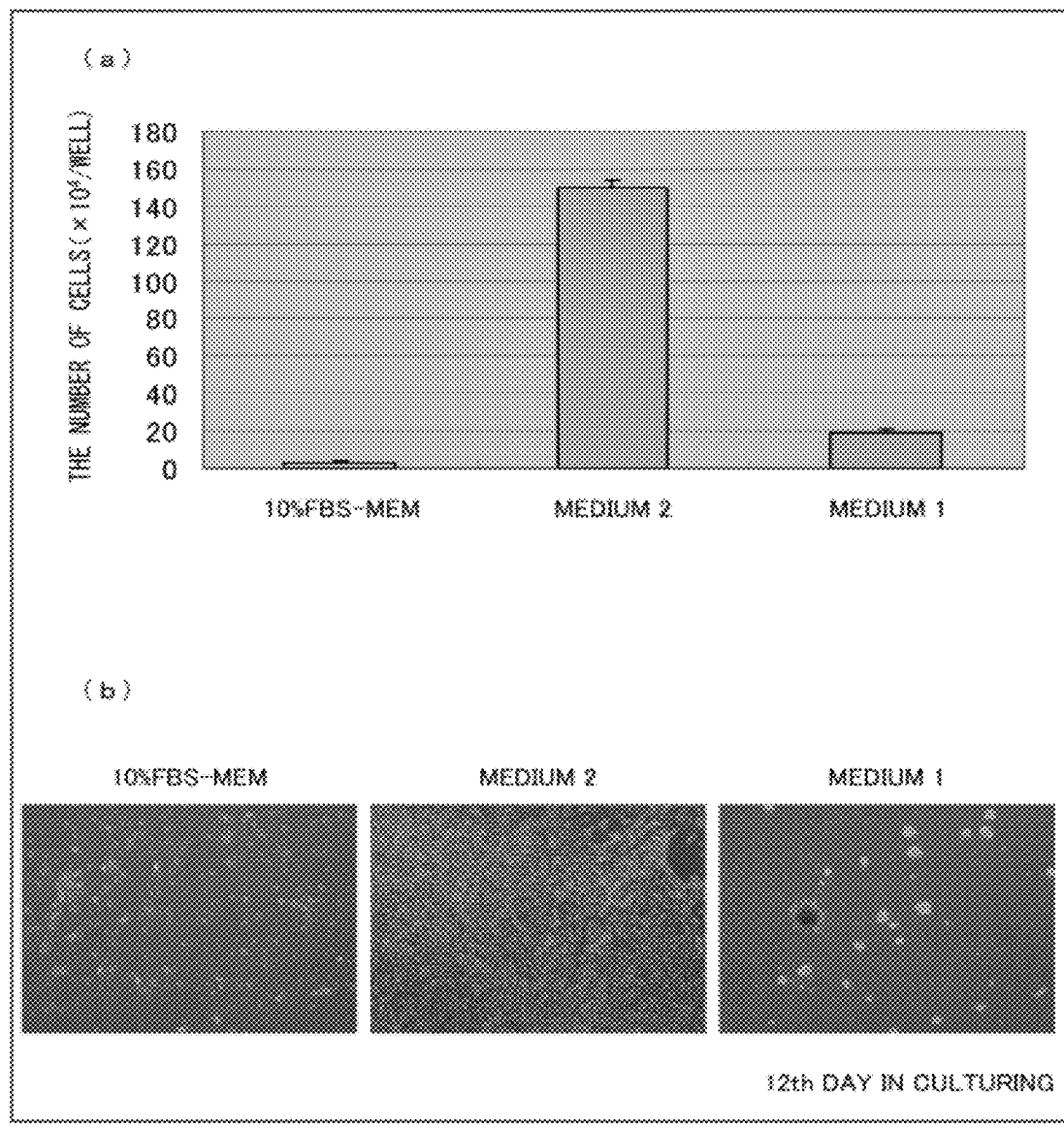
FIG. 8 is a graph and views showing a proliferation promoting effect of a medium 1 and a medium 2 on hMSCs derived from an initial synovial membrane: (a) of FIG. 8 is a graph showing the number of cells of hMSCs derived from a synovial membrane (on the twelfth day in culturing); and (b) of FIG. 8 is views each illustrating a state of the proliferated hMSCs derived from the synovial membrane (on the twelfth day in the culturing).

(3. Result)
Results are shown in FIG. 8. FIG. 8 is a graph and views showing a proliferation promoting effect of a medium 1 and a medium 2 on an initial synovial membrane derived hMSCs: (a) of FIG. 8 is a graph showing the number of synovial membrane derived hMSCs on the twelfth day in the culturing; and (b) of FIG. 8 is views each illustrating a proliferated state of the synovial membrane derived hMSCs on the twelfth day in the culturing. In (b) of FIG. 8, the synovial membrane derived hMSCs were observed with a magnification of ten times.

It was confirmed that, as shown in (a) of FIG. 8, the medium 2 had a remarkably high proliferation promoting effect on the initial synovial membrane derived hMSCs (eight times as many as a case of using the medium 1: forty times or more as many as a case of using the 10% FBS containing DMEM).

Example 5

The following experiment was carried out.
(1. Cell Culture)
Mesenchymal stem cells derived from a human synovial membrane (synovial membrane derived hMSCs) were separated by the processes (i) to (iii) described in the above item "1. Cell culture" of Example 4.

The initial synovial membrane derived hMSCs obtained by centrifugation were cultured by use of the medium 2 for eleven days, and then were cultured in the following medium.

10% FBS containing DMEM (10% FBS-DMEM) (SIGMA® D6046, FBS; HYCLONE®, PS(+)).
  medium 1
  medium 2

The initial synovial membrane derived hMSCs were cultured in a carbon dioxide incubator (95% air and 5% $CO_2$) at 37° C.

Figure 9:
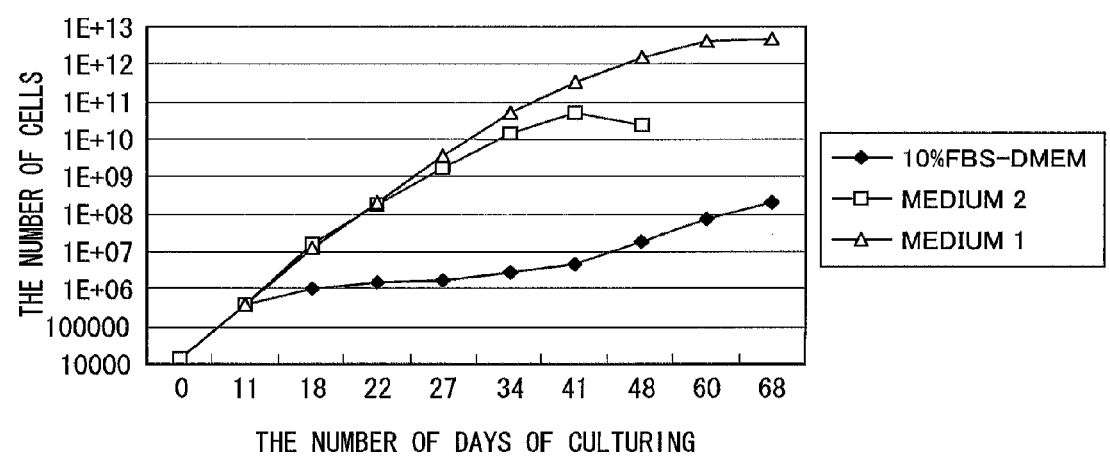
FIG. 9 is a graph showing a chronological change of the number of cells over a period from 0 day (start of culturing) to 68 days.

(2. Cell Proliferation Measurement)
The number of cells was measured by a coulter counter.
(3. Result)
A result was shown in FIG. 9. FIG. 9 is a graph showing a chronical change of the number of synovial membrane derived hMSCs during a period from the 0 day to sixty-eighth day.

It was confirmed that, as shown in the graph of FIG. 9, the synovial membrane derived hMSCs were efficiently amplified by culturing the initial synovial membrane derived hMSCs in the medium 2 and then culturing the synovial membrane derived hMSCs in the medium 1 (on the forty-eighth day in culturing, the synovial membrane derived hMSCs were hundred thousand times as many as those cultured in a 10% FBS-DMEM from the eleventh day in the culturing, and were ten thousand times as many as those cultured in the medium 2 during the period from the 0 day to sixty-eighth day).

Example 6

The following experiment was carried out.
(1. Cell Culture)
Mesenchymal stem cells derived from a human synovial membrane (synovial membrane derived hMSCs) were separated by the processes (i) to (iii) described in the above item "1. Cell culture" of Example 4.

In order to separate and proliferate the synovial membrane derived hMSCs, the synovial membrane derived hMSCs obtained by centrifugation were moved to a flask, and were cultured in the medium 2 from primary cell culture (P0) to third cell culture (P3), then were cultured in the medium 1 shown in Table 1 from primary cell culture (P0) to fourth cell culture (P4). The synovial membrane derived hMSC was cultured in a carbon dioxide incubator (95% air and 5% $CO_2$) at 37° C.

The medium was changed twice a week while the synovial membrane derived hMSCs were cultured. Those cells were subcultured every 7 to 21 days. Amplification of the synovial membrane derived hMSCs was performed by inoculating mesenchymal stem cells ($1\sim2\times10^4$) thereof in the medium (1 ml) at 37° C. under a 5% $CO_2$ culture condition.

(2. Result)
Synovial membrane tissues (1 g) were proliferated to an amount for 1,000 persons (the maximum number of transplanted cells of osteoarithropathy: $1.5\times10^9$) in three to four weeks by culturing the synovial membrane tissues in the medium 2 and the medium 1 in combination.

Example 7

The following experiment was carried out.
(Flask)
The following flasks were used.
  Flask 1: 75 $cm^2$ flask (Falcon)
  Flask 2: 75 $cm^2$ flask (manufactured by SUMITOMO BAKELITE CO., LTD.)
(Culture Fluid)
The following liquid media were used.
  10% FBS containing DMEM (10% FBS-DMEM) (sigma D6046, FBS; Hyclone, PS(+))
  medium 1
  medium 1+fibronectin (final concentration 5 μg/mL)
(Cells)
The following mesenchymal stem cells derived from bone marrows (bone marrow derived hMSCs) were used.
  Cells 1 (P2): $1\times10^6$, cells were subcultured on the twelfth day.
  Cells 2 (P3): $1\times10^6$, cells were subcultured on the thirtieth day. proliferation speed is low.
  Cells 3 (P1): $1\times10^6$, cell were subcultured on the twelfth day.

(Culture Method)

The hMSCs derived from bone marrow (cells 1 to cells 3) were cultured under the following condition at inoculation density of 5,000 cells/cm$^2$. Note that, if a culture fluid 3 was used, fibronectin was added when the hMSCs were inoculated.

Condition A: flask 1+10% FBS-DMEM (positive control)
Condition B: flask 1+medium 1
Condition C: flask 1+medium 1+fibronectin
Condition D: flask 2+10% FBS-DMEM (negative control)
Condition E: flask 2+medium 1
Condition F: flask 2+medium 1+fibronectin (2. Cell Proliferation Measurement)

<Cells 1>

Cells were inoculated in a flask when the cells were subcultured three times, and were started to be cultured. A proliferated state of cells was visually observed by the use of an optical microscope on the fifth day of culturing.

<Cells 2>

Cells were inoculated in a flask when the cells were subcultured four times, and were started to be cultured. A proliferated state of cells was visually observed by the use of an optical microscope on the fifth day of culturing.

<Cells 3>

Cells were inoculated in a flask when the cells were subcultured twice, and were started to be cultured. A proliferated state of cells was visually observed by the use of an optical microscope on the fifth day of culturing.

(3. Results)

<Cells 1>

Figure 10:
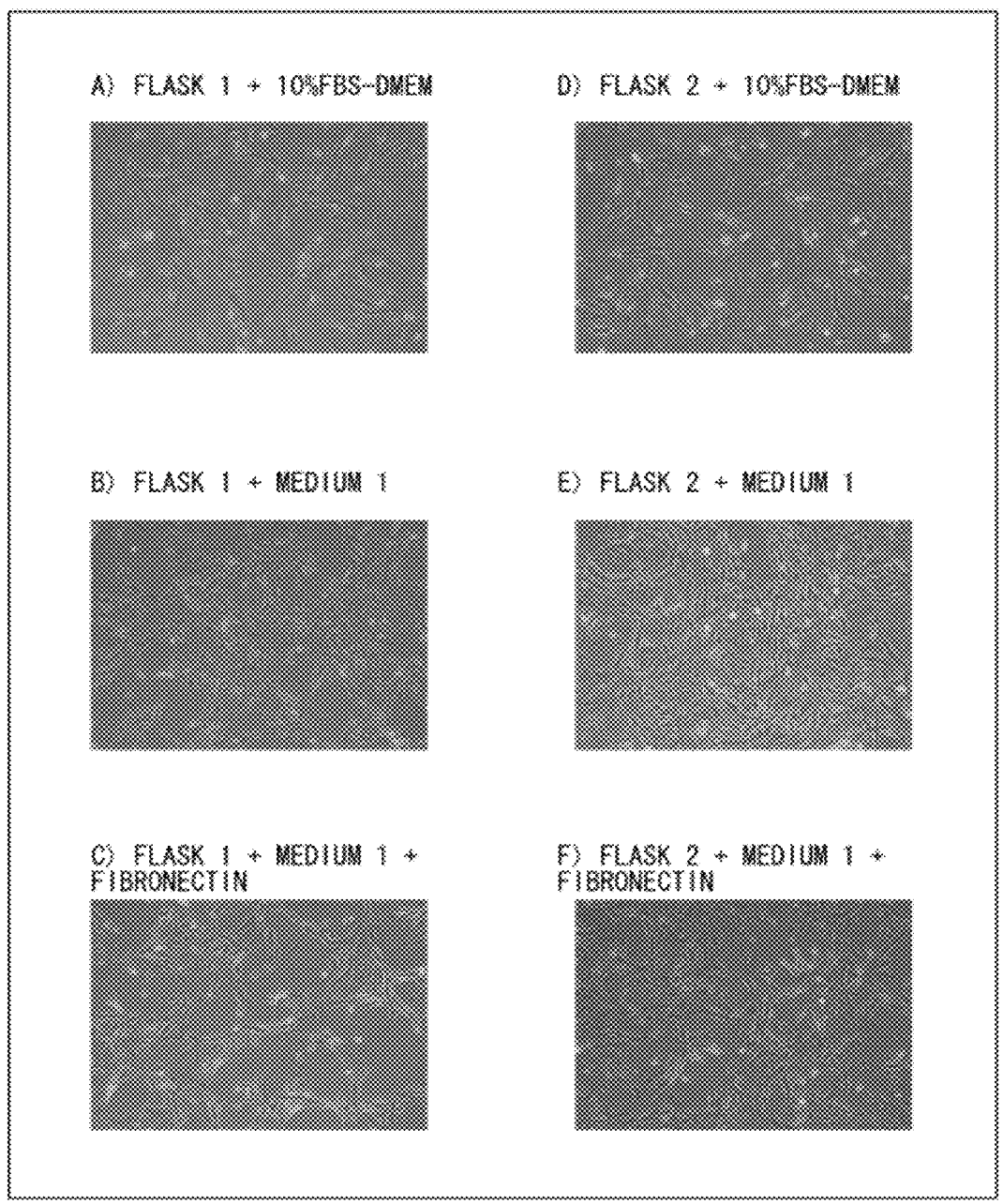
FIG. 10 is views each illustrating a proliferated state of hMSCs (cells 1) derived from bone marrow on the fifth day in culturing.

Results are shown in FIG. 10. FIG. 10 is views each illustrating a proliferated state of hMSCs (cells 1) derived from bone marrow on the fifth day of culturing. In FIG. 10, the bone-marrow derived hMSCs were observed with a magnification of forty times.

As illustrated in FIG. 10, dead cells were found, however, about 30% of cells were found to be adhered under the condition A and the condition D. Further, cells were locally proliferated under the condition B and the condition E. It was found that a state of adhesion between cells cultured under each of the condition B and the condition E was different from a state of adhesion between cells cultured under each of the condition A and the condition D, and about 20% of the cells were adhered under the condition B and the condition E. Further, cells cultured under the condition C and the condition F were similar to those under the condition B and the condition E, i.e., were locally proliferated. It was found that the cells were differently proliferated in each flask under the condition F. However, about 20% of the cells were adhered under the condition F, which is similar to those under the condition B and the condition E.

<Cells 2>

Figure 11:
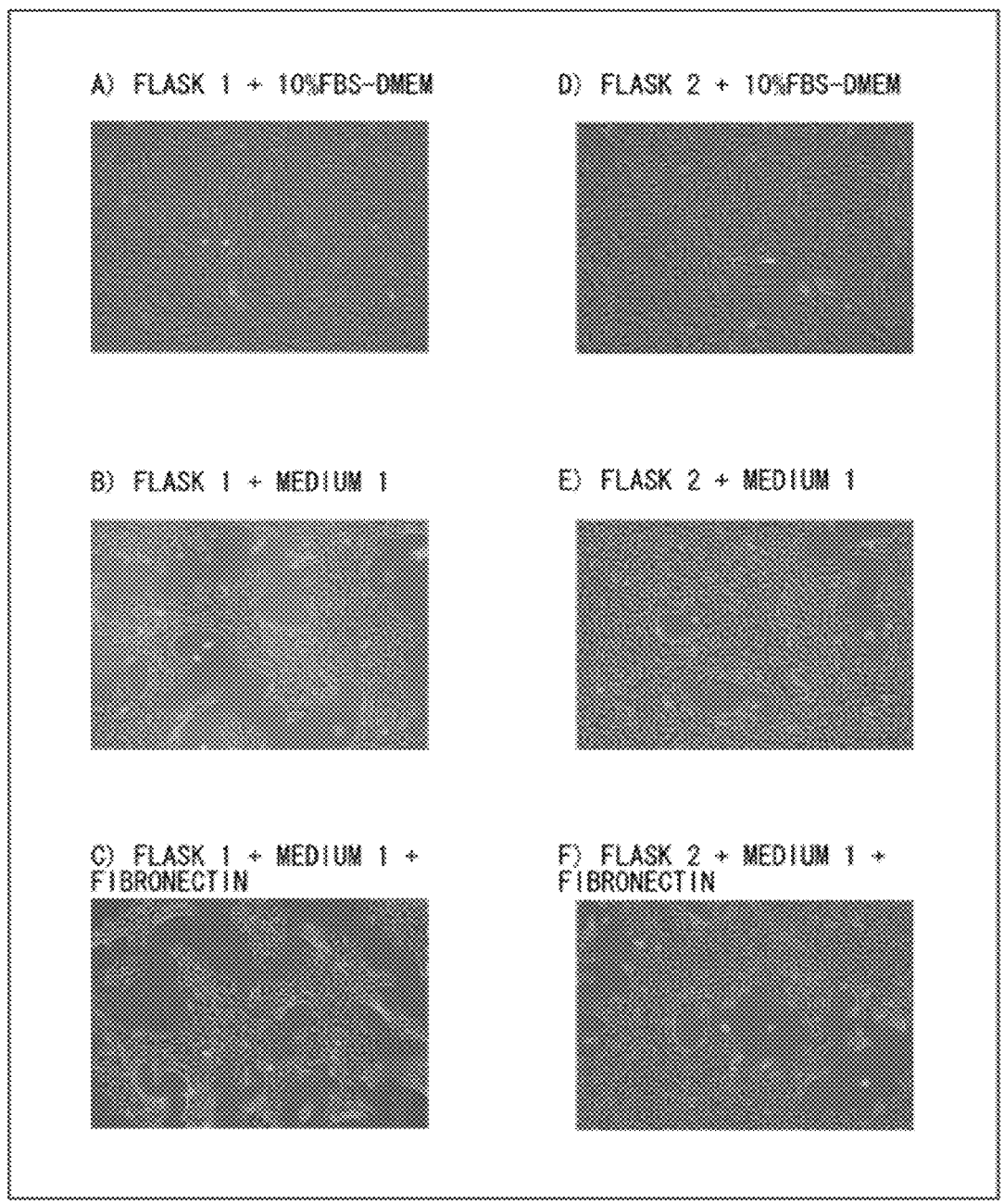
FIG. 11 is views each illustrating a proliferated state of hMSCs (cells 2) derived from bone marrow on the fifth day in culturing.

Results are shown in FIG. 11. FIG. 11 is views each illustrating a proliferated state of hMSCs (cells 2) derived from bone marrow on the fifth day of culturing. In FIG. 11, the bone-marrow derived hMSCs were observed with a magnification of forty times.

As illustrated in FIG. 11, the cells 2 smoothly were proliferated to about 70% of a confluent state under the condition A and the condition D, and the cells thus proliferated under each of the condition A and the condition D entered a satisfactory state. The cells 2 were proliferated to about 70% to 80% of the confluent state under the condition B. The cells were proliferated to about 90% of the confluent state under condition E, i.e., substantially became the confluent state. The cells under the condition B and condition E were atrophied to thereby have spaces such as holes, as compared with those under the condition A and the condition D. Further, the cells 2 were proliferated to 80% of the confluent state under the condition C and the condition F. A state of adhesion between cells under each of the condition C and the condition F was the same as that under each of the condition B and the condition E, however, the number of the cells under each of the condition C and the condition F was slightly less than that under each of the condition B and the condition E.

<Cell 3>

Figure 12:
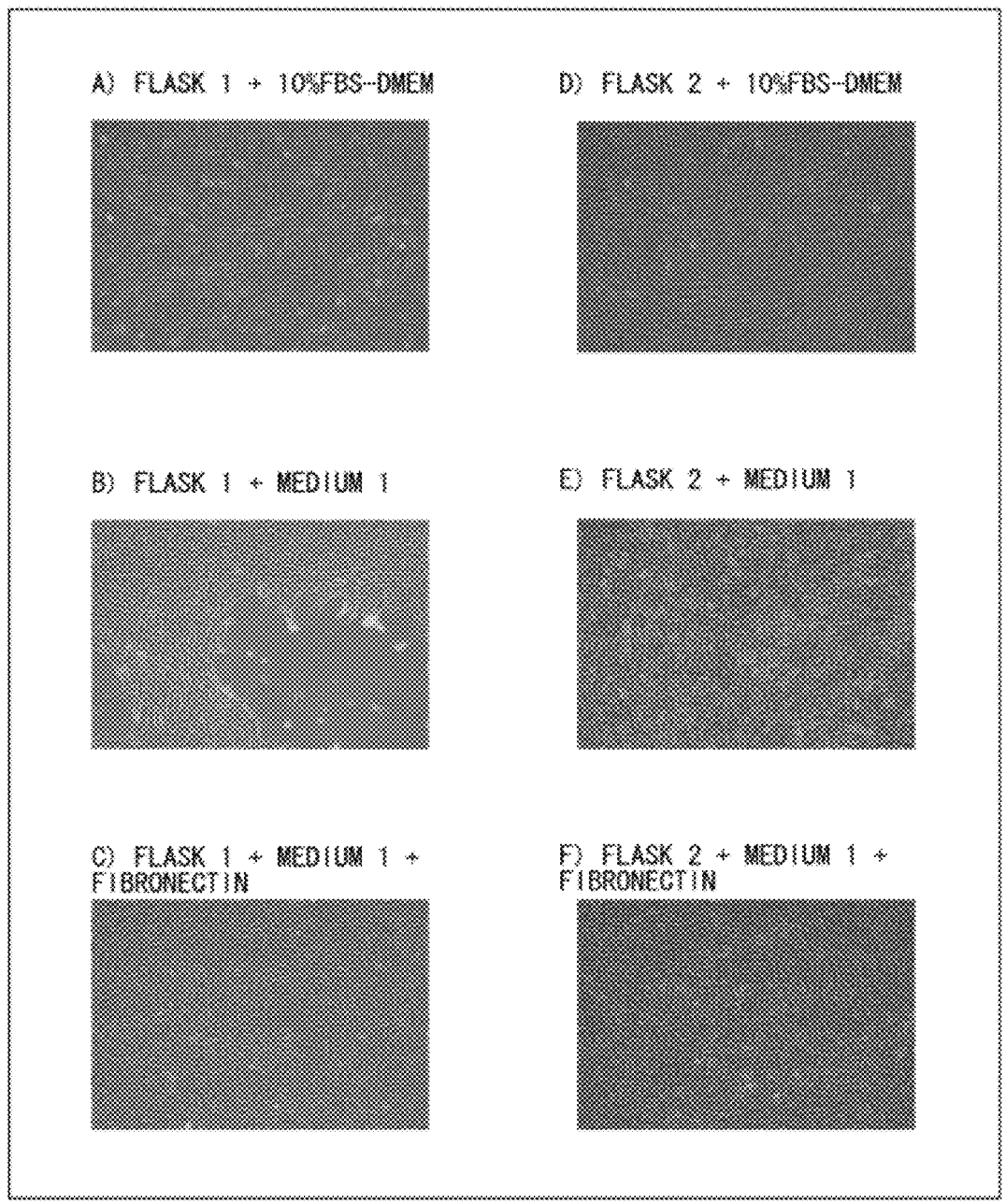
FIG. 12 is views each illustrating a proliferated state of hMSCs (cells 3) derived from bone marrow on the fifth day in culturing.

Results are shown in FIG. 12. FIG. 12 is views each illustrating a proliferated state of bone-marrow derived hMSCs (cells 3) on the fifth day of culturing. In FIG. 12, the bone-marrow derived hMSCs were observed with a magnification of forty times.

As illustrated in FIG. 12, the cell 3 were proliferated to 8090% of the confluent state under the condition A and the condition D, and the cells 3 under each of the condition A and the condition D substantially become the confluent state. Further, it was found that the cells were proliferated to about 80~90% of the confluent state under the condition B and the condition E, except that parts of the cells were peeled off under the condition B. Furthermore, it was found that the cells were not peeled off under the condition C and the condition F, as compared with the condition B and the condition E, and were proliferated to about 90% of the confluent state under each of the condition C and the condition F.

From those results, it was confirmed that, in a case where the condition B and the condition E were compared with each other, the condition E had cell proliferation ability higher than that of the condition B even if any cell strain of the cells 1 to 3 was used. That is, it was confirmed that the flask 2 was more suitable for proliferating the cells 1 to 3 than the flask 1.

It was confirmed that an adhesion rate of the cells was improved by adding fibronectin serving as cell adhesion molecules to the medium, as is clear from the condition C and the condition F.

Example 8

The following experiment was carried out.

(1. Soft Agar Colony Method)

A soft agar medium (DMEM-10% FCS-0.6%-agar) was added to each well of the 96-well-plate, and was gelatinized. Then a soft agar medium (DMEM-10% FCS-0.4%-agar) in which cells were suspended was added to the soft agar medium thus gelatinized. Human chondrosarcoma cell strains (OUMS-27, bought from JCRB Cell Bank) or neonatal normal human dermal fibroblasts (NHDF, bought from Lonza Inc.) was used as the cells, and the number of inoculated cells per well was set to 0~10000. The human chondrosarcoma cell strain is a cell strain whose mesenchymal cell is cancerated. A group in which an serum content of a culture fluid to be added on the soft agar medium was 10% and a group in which the serum content was 20% were prepared. Note that, in this experiment, the serum was added to the culture fluid to form a condition which is considered to help the cells to be proliferated more actively.

The colony was dyed with p-iodonitrotetrazolium Violet (Sigma product.) on the fourteenth day of culturing, and the number of colonies formed in each well was counted under a microscope. A colony having a diameter of 25 μm or more was counted as a formed colony.

(Culture Fluid)

The following liquid media were used. 4.5 g/L containing glucose DMEM (DMEM 4.5 g/L glucose)

medium 1 (see Table 1)

Note that glucose was added in order to form a colony and promote proliferation. Considering a low-concentration glucose medium (1 g/ml) would not favorably facilitate colony formation of the OUMS-27, a high-concentration glucose containing medium (commercial product) was chosen for culturing.

(2. Results)

Figure 13:
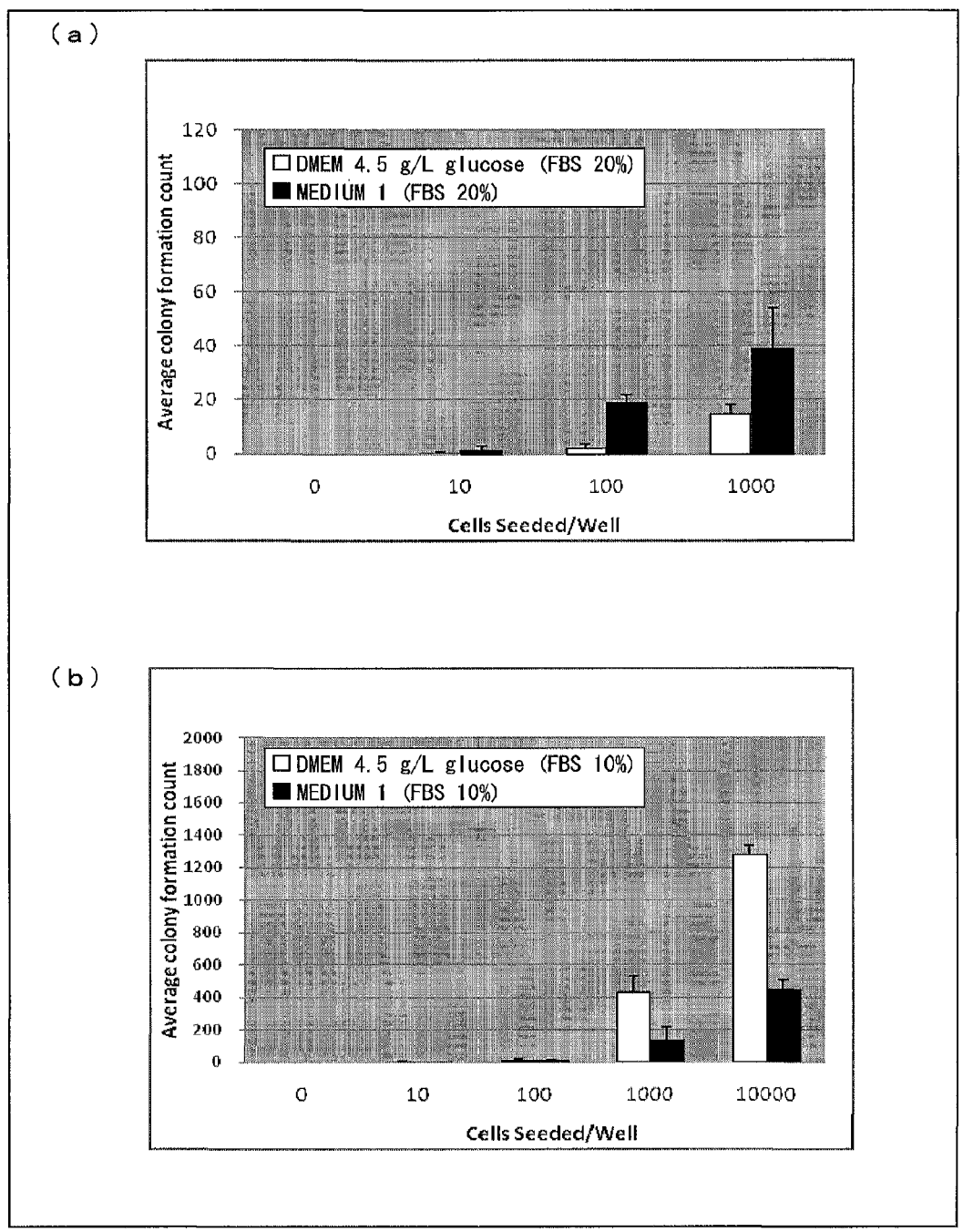
FIG. 13 is a graph showing effects of the medium 1 on proliferation of neonatal normal human dermal fibroblasts and human chondrosarcoma cell strains: (a) of FIG. 13 is a graph showing the number of colonies of the neonatal normal human dermal fibroblasts on the fourteenth day in culturing; and (b) of FIG. 13 is a graph showing the number of colonies of the human chondrosarcoma cell strains on the fourteenth day in culturing.

FIG. 13 is graphs showing effects of the medium 1 on proliferation of the neonatal normal human dermal fibroblasts and the human chondrosarcoma cell strains: (a) of FIG. 13 is a graph showing the number of colonies of the neonatal normal human dermal fibroblasts on the fourteenth day of culturing; (b) of FIG. 13 is a graph showing the number of colonies of the human chondrosarcoma cell strain during a period on the fourteenth day of the culturing. Note that the number of colonies having a size of 25 µm or more is shown in FIG. 13.

As shown in the graph (a) of FIG. 13, the number of colonies were remarkably increased in a case where the neonatal normal human dermal fibroblasts were cultured in the medium 1, as compared with those cultured in DMEM containing 4.5 g/L glucose. Meanwhile, as shown in the graph (b) of FIG. 13, the number of colonies was remarkably decreased in a case where the human chondrosarcoma cell strains (OUMS-7) were cultured in the medium 1, as compared with those cultured in DMEM containing 4.5 g/L glucose.

From this result, it was found that, in a case where the cells were cultured by the use of the medium 1 as a culture fluid, stem cells in the neonatal normal human dermal fibroblasts, i.e., the cells which do not have the tumorigenicity were promoted to be proliferated, meanwhile, proliferation of cells having the tumorigenicity, such as the human chondrosarcoma cell strains, was suppressed. It was therefore found that, by culturing the cells by the use of the medium 1 as the culture fluid, normal cells which do not have the tumorigenicity could be selectively and efficiently proliferated while proliferation of the cell having the tumorigenicity could be selectively suppressed.

Further, from this result, the following was indicated: in a case where another experiment was carried out by the use of the soft agar colony method under the same condition other than a culture fluid and in a case where the number of colonies by the use of DMEM containing 4.5 g/L glucose as the culture fluid was significantly larger than that by the use of the medium 1 as the culture fluid, it was determined that the cells were characterized by the ability to produce tumors; and, in a case where the number of the colonies by the use of DMEM containing 4.5 g/L glucose as the culture fluid was significantly smaller than that by the use of the medium 1 as the culture fluid, it was determined that the cells were characterized by the inability to produce tumors.

The present invention is not limited to the description of the embodiments above, and can be modified in numerous ways by a skilled person as long as such modification falls within the scope of the claims. An embodiment derived from a proper combination of technical means disclosed in different embodiments is also encompassed in the technical scope of the present invention.

INDUSTRIAL APPLICABILITY

The present invention provides a transplantation treatment material having safer and higher useful mesenchymal stem cells. Therefore, the present invention is suitably applicable to a regenerative medicine for a transplantation treatment etc. by the use of mesenchymal stem cells.

The invention claimed is:

1. A method for producing a cell preparation containing mesenchymal stem cells, comprising the steps of:

a proliferation step comprising proliferating mesenchymal stem cells in a serum-free medium containing a fibroblast growth factor (FGF), a platelet derived growth factor (PDGF), a transforming growth factor-β (TGF-β), a hepatocyte growth factor (HGF), an epidermal growth factor (EGF), at least one phospholipid, and at least one fatty acid; and a screening step comprising screening mesenchymal stem cells whose immunosuppression ability is maintained or improved, from the mesenchymal stem cells thus proliferated in the proliferation step; and a pre-proliferation step comprising before the proliferation step, culturing the mesenchymal stem cells in a serum-free medium B containing a FGF, a PDGF, an EGF, at least one phospholipid, and at least one fatty acid, the serum-free medium B does not contain a HGF and a TGF-β, a culture time period of the pre-proliferation step and the proliferation step being 48 days to 68 days, and the cell preparation comprises the mesenchymal stem cells whose immunosuppression ability is maintained or improved;

wherein the mesenchymal stem cells are subcultured at least once in the pre-proliferation step.

2. A method according to claim 1, further comprising, before the screening step, the step of:

a serum culturing step comprising culturing, in a medium containing serum, the mesenchymal stem cells which have been subjected to the proliferation step.

3. A method according to claim 1, further comprising the step of:

a second screening step comprising screening the mesenchymal stem cells which do not have tumorigenicity, from the mesenchymal stem cells proliferated in the proliferation step.

4. The method according to claim 1, wherein in the proliferation step, the mesenchymal stem cells are proliferated by use of a culture vessel suitable for proliferation of the mesenchymal stem cells.

5. A method according to claim 1, wherein the serum-free medium further contains cell adhesion molecules in the proliferation step.

6. The method according to claim 1, wherein:

the mesenchymal stem cells are subcultured at least once in the proliferation step.

7. The method according to claim 6, wherein:

in the proliferation step, the subculturing is performed in such a way that the mesenchymal stem cells are peeled off by use of a cell removing agent which does not contain a component derived from a mammal or a microorganism.

8. A method according to claim 4, further comprising, before the proliferation step, the step of:

selecting the culture vessel suitable for the proliferation of the mesenchymal stem cells.

9. The method according to claim 1, wherein:

the phospholipid is selected from the group consisting of phosphatidic acid, lysophosphatidic acid, phosphatidylinositol, phosphatidyl serine, phosphatidyl ethanolamine, phosphatidyl choline, and phosphatidyl glycerol.

10. The method according to claim 1, wherein:
the fatty acid is selected from the group consisting of linoleic acid, oleic acid, linolenic acid, arachidonic acid, myristic acid, palmitoleic acid, palmitic acid, and stearic acid.

* * * * *